United States Patent [19]

Venet et al.

[11] Patent Number: 5,028,606

[45] Date of Patent: Jul. 2, 1991

[54] (1H-AZOL-1-YLMETHYL)SUBSTITUTED QUINOXALINE DERIVATIVES

[75] Inventors: Marc G. Venet, Paris; Gerard C. Sanz, Garges les Gonesse, both of France; Alfons H. M. Raeymaekers, Beerse; Eddy J. E. Freyne, Rumst, both of Belgium

[73] Assignee: Janssen Pharmaceutica N.V., Beerse, Belgium

[21] Appl. No.: 434,957

[22] Filed: Nov. 13, 1989

[30] Foreign Application Priority Data

Nov. 29, 1988 [GB] United Kingdom ............... 8827822

[51] Int. Cl.$^5$ ............... A61K 31/495; C07D 403/08; C07D 403/10; C07D 403/14
[52] U.S. Cl. ................... 514/249; 544/353; 544/354; 544/355; 544/356
[58] Field of Search ............. 544/353, 354, 356, 355; 514/249

[56] References Cited

U.S. PATENT DOCUMENTS

| 3,870,718 | 3/1975 | Abuel-Haj | 544/353 |
| 4,756,999 | 7/1988 | Swain et al. | 544/353 |
| 4,853,400 | 8/1989 | Parsons et al. | 544/356 |
| 4,859,684 | 8/1989 | Raeymaekers et al. | 514/314 |

OTHER PUBLICATIONS

Chytil, *Pharmacological Reviews*, 36, p. 935 (1984).
Elias et al., *Arch. Dermatol.*, 117, p. 160 (1981).
Lotan, *Biochimica et Biophysica Acta*, 605, p. 33 (1980).
Thomas et al., *J. Am. Acad. Dermatol.*, 4, p. 505 (1981).
Goodman, *The New England Journal of Medicine*, 16, p. 1023 (1984).

*Primary Examiner*—Cecilia Shen
*Assistant Examiner*—E. Beinhardt
*Attorney, Agent, or Firm*—Charles J. Metz

[57] ABSTRACT (1H-azol-1-ylmethyl)substituted quinoxaline derivatives, compositions containing the same, and methods of treating mammals suffering from disorders which are characterized by an increased proliferation and/or abnormal differentiation of epithelial tissues.

13 Claims, No Drawings

(1H-AZOL-1-YLMETHYL)SUBSTITUTED QUINOXALINE DERIVATIVES

BACKGROUND OF THE INVENTION

In the European Patent Application No. 260,744, published Mar. 3, 1988, which corresponds to U.S. Pat. No. 4,859,684, there are described (1H-azol-1-ylmethyl) substituted benzimidazole derivatives which compounds are useful as androgenic hormone biosynthesis inhibitors. The compounds of the present invention differ from the cited art compounds by the fact that they contain a quinoxaline moiety in place of a benzimidazole moiety and by their favourable pharmaceutical properties. In particular the compounds of the invention suppress the plasma elimination of retinoic acids. Further it was found that some compounds of the invention inhibit the formation of androgens from progestines and/or inhibit the action of the enzyme complex aromatase which catalyses the formation of estrogens from androgenic steroids in mammals.

DESCRIPTION OF THE INVENTION

The present invention is concerned with novel compounds of formula

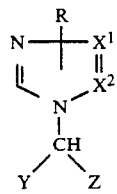
(I)

the pharmaceutically acceptable acid addition salts thereof and the stereochemically isomeric forms thereof, wherein —$X^1=X^2$— is a bivalent radical having the formula

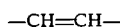 (x),

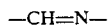 (y), or

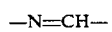 (z);

R is hydrogen or $C_{1-6}$alkyl;
Y is hydrogen; $C_{1-10}$alkyl; $C_{3-7}$cycloalkyl; $Ar^1$; $Ar^2$-$C_{1-6}$alkyl; $C_{2-6}$alkenyl or $C_{2-6}$alkynyl;
Z is a radical of formula

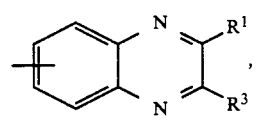 (a-1),

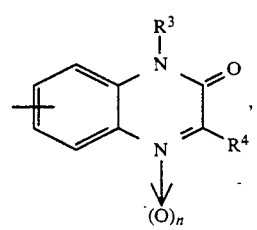 (a-2)

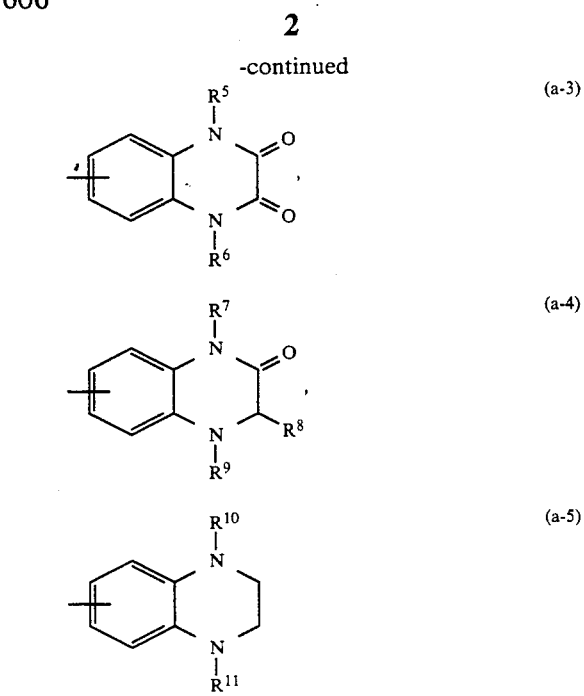

wherein
$R^1$ is hydrogen, halo, $C_{1-6}$alkyl, $C_{1-6}$alkyloxy, amino, mono- or di($C_{1-6}$alkyl)amino, $Ar^2$ or imidazolyl;
$R^2$ is hydrogen, $C_{1-6}$alkyl or $Ar^1$;
$R^3$ and $R^7$ each independently are hydrogen, $C_{1-6}$alkyl, $Ar^2$-$C_{1-6}$alkyl, amino or mono ($C_{1-6}$alkyl)amino;
$R^4$ and $R^8$ each independently are hydrogen, $C_{1-6}$alkyl, $Ar^1$, $C_{1-6}$alkylcarbonyl, $Ar^2$-carbonyl, $C_{1-6}$alkyloxycarbonyl, carboxyl, $C_{1-6}$alkyloxycarbonyl$C_{1-4}$alkyl, aminocarbonyl or cyano;
$R^5$, $R^6$, $R^9$, $R^{10}$ and $R^{11}$ each independently are hydrogen, $C_{1-6}$alkyl or $Ar^2$-$C_{1-6}$alkyl;
n is 0 or 1; and
$Ar^1$ is phenyl, substituted phenyl, naphthalenyl, pyridinyl, imidazolyl, triazolyl, thienyl, furanyl or thiazolyl and $Ar^2$ is phenyl or substituted phenyl; said substituted phenyl in $Ar^1$ or $Ar^2$ being phenyl substituted with 1, 2 to 3 substituents each independently selected from halo, hydroxy, trifluoromethyl, $C_{1-6}$alkyl, $C_{1-6}$alkyloxy, cyano, amino, mono- and di($C_{1-6}$alkyl)amino, nitro, carboxyl, formyl and $C_{1-6}$alkyloxycarbonyl.

As used in the foregoing definitions the term halo is generic to fluoro, chloro, bromo and iodo; the term "$C_{1-6}$alkyl" is meant to include straight chained and branched saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-10}$alkyl" is meant to include the higher homologs of "$C_{1-6}$alkyl" containing 1-10 carbon atoms; the term "$C_{3-7}$cycloalkyl" is generic to cyclopropyl, cyclobutyl, cyclopentyl, cyclohexyl and cycloheptyl; "$C_{2-6}$alkenyl" defines straight chained and branched hydrocarbon radicals containing one double bond having from 2 to 6 carbon atoms such as, for example, ethenyl, 2-propenyl, 3-butenyl, 2-butenyl, 2-pentenyl, 3-pentenyl, 3-methyl-2-butenyl and the like; "$C_{2-6}$alkynyl" defines straight chained and branched hydrocarbon radicals containing one triple bond and having from 2 to 6 carbon atoms such as, for example, 2-propynyl, 2-butynyl, 3-butynyl, 2-pentynyl, 3-pentynyl, 4-pentynyl and the like.

It is to be understood that the

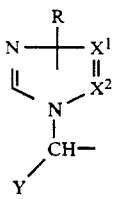

moiety hereinafter referred as the 1H-azol-1-ylmethyl moiety may be substituted on either the 5, 6, 7 or 8 position of the bicyclic ring system, the 6 or 7 position being preferred.

Further it should be noted that the compounds of formula (I) wherein Z is a radical of formula (a-1) are denoted as compounds of formula (I-a-1); compounds of formula (I) wherein Z is a radical of formula (a-2) are denoted as compounds of formula (I-a-2); compounds of formula (I) wherein Z is a radical of formula (a-3) are denoted as compounds of formula (I-a-3); compounds of formula (I) wherein Z is a radical of formula (a-4) are denoted as compounds of formula (I-a-4); and compounds of formula (I) wherein Z is a radical of formula (a-5) are denoted as compounds of formula (I-a-5).

The acid addition salts as mentioned hereinabove are meant to comprise the therapeutically active non-toxic acid addition salt forms which the compounds of formula (I) are able to form. The latter can conveniently be obtained by treating the base form with appropriate acids such as, for example, inorganic acids, such as hydrohalic acid, e.g. hydrochloric, hydrobromic and the like, and sulfuric acid, nitric acid, phosphoric acid and the like; or organic acids such as, for example, acetic, hydroxyacetic, propanoic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form. The term acid addition salt also comprises the hydrates and solvent addition forms which the compounds of formula (I) are able to form. Examples of such forms are e.g. hydrates, alcoholates and the like.

From formula (I) it is evident that the compounds of this invention may have several asymmetric carbon atoms in their structure. Pure isomeric forms of the compounds of formula (I) can be separated from the mixture by conventional separation methods. Preferably, if a specific stereoisomer is desired, said compound will be synthesized by stereoselective methods of preparation. These methods will advantageously employ enantiomerically pure starting materials.

Further it is evident that the compounds of formula (I) may also contain in their structure a tautomeric system and consequently these compounds can be present in each of their tautomeric forms.

Particular compounds of the present invention are those compounds of formula (I) wherein R is hydrogen or $C_{1-4}$alkyl; and/or Y is hydrogen, $C_{1-6}$alkyl, $C_{3-7}$cycloalkyl, phenyl, substituted phenyl, pyridinyl, imidazolyl or thienyl; and/or Z is a radical of formula (a-1), (a-2), (a-3), (a-4) or (a-5) wherein $R^1$ is hydrogen, $C_{1-4}$alkyl, halo, $C_{1-4}$alkyloxy, amino, mono- or di($C_{1-4}$alkyl)amino, phenyl, substituted phenyl or imidazolyl, $R^2$ is hydrogen, $C_{1-4}$alkyl, phenyl or substituted phenyl, $R^3$ is hydrogen, $C_{1-4}$alkyl, amino, $C_{1-4}$alkylamino or $C_{1-4}$alkyl substituted with phenyl or substituted phenyl; $R^4$ is hydrogen, $C_{1-4}$alkyl, $C_{1-4}$alkyloxycarbonyl$C_{1-4}$alkyl, phenyl, substituted phenyl, carboxyl, $C_{1-4}$alkyloxycarbonyl, carboxylyl, phenylcarbonyl, substituted phenylcarbonyl, naphthalenyl, thienyl, furanyl, pyridinyl or imidazolyl; $R^5$ and $R^6$ each independently are hydrogen or $C_{1-4}$alkyl; $R^7$ is hydrogen, $C_{1-4}$alkyl, amino or $C_{1-4}$alkyl substituted with phenyl or substituted phenyl; $R^8$ is hydrogen, $C_{1-4}$alkyl, phenyl, substituted phenyl, $C_{3-7}$cycloalkyl, naphthalenyl, thienyl, pyridinyl or imidazolyl; $R^9$ is hydrogen or $C_{1-4}$alkyl and $R^{10}$ and $R^{11}$ are hydrogen.

More particular compounds are those particular compounds wherein $-X^1=X^2-$ is a radical having the formula (x) or (y); and/or R is hydrogen; and/or Y is hydrogen, $C_{1-4}$alkyl, cyclopropyl, cyclopentyl, cyclohexyl, imidazolyl, thienyl, pyridinyl or phenyl optionally substituted with one or two substituents selected from halo, $C_{1-4}$alkyl, $C_{1-4}$alkyloxy and trifluoromethyl.

Among the compounds of the aforementioned subgroups special emphasis is put on compounds of formula (I) wherein Z is a radical of formula (a-1) wherein $R^1$ is hydrogen, $C_{1-4}$alkyl, $C_{1-4}$alkyloxy, halo, amino, di($C_{1-4}$alkyl)amino, phenyl or imidazolyl, $R^2$ is hydrogen, $C_{1-4}$alkyl or phenyl and Y is hydrogen, $C_{1-4}$alkyl, thienyl, imidazolyl or phenyl optionally substituted with one or two substituents selected from halo, $C_{1-4}$alkyl, $C_{1-4}$alkyloxy or trifluoromethyl; and compounds of formula (I) wherein Z is a radical of formula (a-2) wherein $R^3$ is hydrogen, $C_{1-4}$alkyl, amino or $C_{1-4}$alkyl substituted with phenyl and $R^4$ is hydrogen, $C_{1-4}$alkyl, carboxyl, $C_{1-4}$alkyloxycarbonyl, naphthalenyl, thienyl, pyridinyl, imidazolyl, phenyl or phenyl substituted with 1, 2 or 3 substituents each independently selected from $C_{1-4}$alkyl, $C_{1-4}$alkyloxy, halo, hydroxy and trifluoromethyl and Y is hydrogen, $C_{1-4}$alkyl, cyclopropyl, cyclopentyl, cyclohexyl, imidazolyl, thienyl, pyridinyl or phenyl optionally substituted with one or two substituents selected from halo, $C_{1-4}$alkyl, $C_{1-4}$alkyloxy and trifluoromethyl.

Preferred compounds of formula (I) wherein Z is a radical of formula (a-1) are those compounds wherein $-X^1=X^2-$ is a radical having the formula (x) or (y); R is hydrogen; $R^1$ and $R^2$ are both hydrogen and Y is phenyl, halophenyl or thienyl.

Most preferred compounds of formula (I) wherein Z is a radical of formula (a-1) are selected from 6-[(1H-imidazol-1-yl)phenylmethyl]quinoxaline and 6-[(4-fluorophenyl) (1H-imidazol-1-yl)methyl]quinoxaline, the pharmaceutically acceptable acid addition salts and possible stereochemically isomeric forms thereof.

Preferred compounds of formula (I) wherein Z is a radical of formula (a-2) are those compounds wherein $-X^1=X^2-$ is a radical of formula (x) or (y); R is hydrogen; Y is hydrogen, $C_{1-4}$alkyl, cyclopropyl, cyclopentyl or cyclohexyl; $R^3$ is hydrogen; $R^4$ is hydrogen, $C_{1-4}$alkyl, naphthalenyl, thienyl, pyridinyl, imidazolyl, phenyl or phenyl substituted with 1 or 2 substituents each independently selected from methyl, halo, hydroxy and methoxy; and n is 0.

Other preferred compounds of formula (I) wherein Z is a radical of formula (a-2) are those compounds wherein —$X^1$=$X^2$— is a radical of formula (x) or (y); Y is phenyl or halophenyl; $R^3$ is hydrogen; $R^4$ is hydrogen or $C_{1-4}$alkyl and n is 0.

Most preferred compounds of formula (I) wherein Z is a radical of formula (a-2) are selected from 6-[1-(1H-imidazol-1-yl)-2-methylpropyl]-3-phenyl-2(1H)-quinoxalinone, 6-[1-(1H-imidazol-1-yl)-2-methylpropyl]-3-propyl-2(1H)-quinoxalinone, 3-(3-fluoro phenyl)-6-[1-(1H-imidazol-1-yl)-2-methylpropyl]-2(1H)-quinoxalinone, the pharmaceutically acceptable acid addition salts and possible stereochemically isomeric forms thereof.

The compounds of formula (I) can be prepared by N-alkylating an azole of formula (II) or an alkali metal salt thereof with a quinoxaline derivative of formula (III).

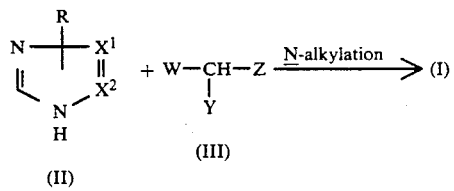

In formula (III) W represents an appropriate reactive leaving group such as, for example, halo, e.g., fluoro, chloro, bromo, iodo or a sulfonyloxy group, e.g. 4-methylbenzenesulfonyloxy, benzenesulfonyloxy, 2-naphthalenesulfonyloxy, methanesulfonyloxy, trifluoromethanesulfonyloxy and the like reactive leaving groups.

The above described N-alkylation is conveniently carried out by stirring the reactants in the presence of a suitable solvent such as, for example, an aromatic hydrocarbon, e.g. benzene, methylbenzene, dimethylbenzene, and the like; an ester, e.g. ethyl acetate, γ-butyrolacetone and the like; a ketone, e.g. 2-propanone, 4-methyl-2-pentanone and the like; an ether, e.g. 1,4-dioxane, 1,1′-oxybisethane, tetrahydrofuran and the like; a polar aprotic solvent, e.g. N,N-dimethylformamide, N,N-dimethylacetamide, dimethyl sulfoxide, 1-methyl-2-pyrrolidinone, acetonitrile, hexamethylphosphor triamide, 1,3-dimethyl-3,4,5,6-tetrahydro-2(1H)-pyrimidinone,1,3-dimethyl-2-imidazolidinone, benzonitrile and the like; or a mixture of such solvents. Somewhat elevated temperatures may be appropriate to enhance the rate of the reaction and in some cases the reaction may even be carried out at the reflux temperature of the reaction mixture. The addition of an appropriate base such as, for example, an alkali or an earth alkaline metal carbonate, hydrogen carbonate, hydroxide, amide or hydride, e.g. sodium hydroxide, potassium hydroxide, potassium carbonate, sodium hydride and the like or an organic base, such as, for example, N,N-dimethyl-4-pyridinamine, pyridine, N,N-diethylethanamine or N-(1-methylethyl)-2-propanamine may be employed to pick up the acid which is liberated during the course of the reaction. In some instances it may be advantageous to use an excess of the azole (II) or to convert the azole first into a suitable salt form thereof such as, for example, an alkali or earth alkaline metal salt, by reacting (II) with an appropriate base as defined hereinabove and subsequently using said salt form in the reaction with the alkylating reagent of formula (III). Additionally, it may be advantageous to conduct said N-alkylation reaction under an inert atmosphere such as, for example, oxygen-free argon or nitrogen gas. Said alkylation may also be carried out by applying art-known conditions of phase transfer catalysis reactions.

Compounds of formula (I) wherein —$X^1$=$X^2$— is a bivalent radical of formula (x), said compounds being represented by formula (I-x), may also be prepared by reacting a quinoxaline of formula (III) with a 1-protected imidazole of formula (II-x) following the N-alkylation procedures described hereinabove for the preparation of compounds of formula (I) starting from (II) and (III).

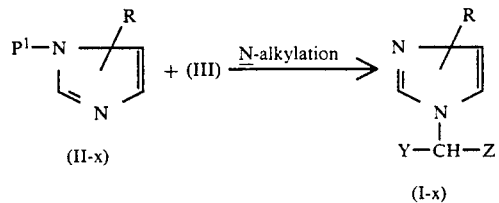

In (II-x) $P^1$ represents a protective group such as, for example, $C_{1-6}$alkylcarbonyl, $C_{1-6}$alkyloxycarbonyl, arylcarbonyl or a tri($C_{1-6}$alkyl)silyl group. In some instances the reaction of (II-x) with (III) first yields a 1-protected imidazolium salt of formula (IV) which may in situ, or if desired, after isolating and further purifying it, be deprotected by stirring it in an aqueous basic solution or acidic solution.

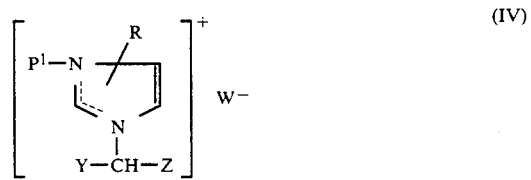

In (IV) $W^-$ is an anion arising from an acid such as, for example, hydrochloric acid, hydrobromic acid, methanesulfonic acid, 4-methylbenzenesulfonic acid and the like acids.

Compounds of formula (I) wherein —$X^1$=$X^2$— is a bivalent radical of formula (y), said compounds being represented by formula (I-y), can also be prepared by endo-N-alkylation of a triazolamine of formula (II-y) with a quinoxaline of formula (III) and subsequent deamination of the thus prepared triazolium salt, wherein $W^-$ is an anion as defined hereinabove.

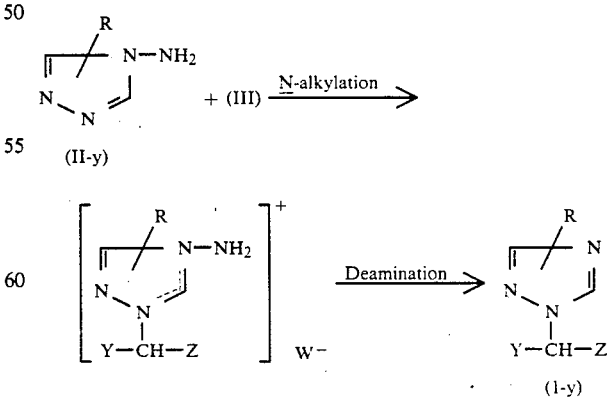

The endo-N-alkylation reaction of (II-y) with (III) is carried out according to similar procedures as described hereinabove for the preparation of a compound of formula (I) starting from (III) and (II). Said deamination reaction is conveniently conducted by reaction with an acidic nitrite solution in the presence of an appropriate reductant, or by reaction with an alkylnitrite such as, for example, 1,1-dimethylethylnitrite or isoamylnitrite and the like. Preferably, said deamination reaction is conducted with an aqueous solution of nitrous acid or of a nitrite salt in a suitable acid in the presence of a reducing agent such as, for example, hypophosphorous acid, formic acid, at a lower temperature.

The compounds of formula (I) may also be prepared by reacting an intermediate of formula (V) with a reagent of formula (VI) such as, for example, a 1,1'-carbonylbis[1H-imidazole], 1,1'-carbonylbistriazole.

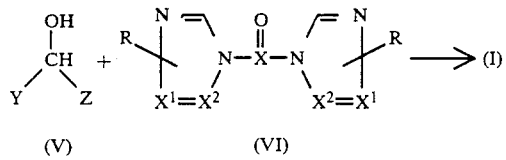

In (VI) X represents C or S.

Said reaction may conveniently be conducted in a suitable solvent such as, for example, an ether, e.g. 1,4-dioxane, tetrahydrofuran; a halogenated hydrocarbon, e.g. di- or trichloromethane; a hydrocarbon, e.g. benzene, methylbenzene, dimethylbenzene; N,N-dimethylformamide, N,N-dimethylacetamide, or a mixture of such solvents. In order to enhance the reaction rate, it may be advantageous to heat the reaction mixture.

The compounds of formula (I) may also be prepared by reacting a ketone or aldehyde of formula (VII) with an azole (II) in the presence of formic acid or formamides as reducing agents.

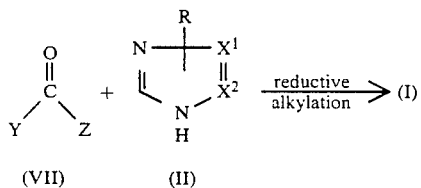

Said reductive alkylation can conveniently be conducted by stirring and heating the reagents in formic acid or formamides optionally in the presence of an acid catalyst. An appropriate acid catalyst for using in this reaction is for example a mineral acid such as, hydrochloric acid, sulfuric acid or a sulfonic acid such as, methanesulfonic acid, benzenesulfonic acid, 4-methylbenzenesulfonic acid and the like. It may be appropriate to remove the water which is formed during the reaction by azeotropical distillation, distillation, complexation and the like methods.

In all of the foregoing and following preparations, the reaction products may be isolated from the reaction mixture and, if necessary, further purified according to methodologies generally known in the art such as, for example, extraction, distillation, crystallization, trituration and chromatography.

The compounds of formula (I) can alternatively be prepared under similar conditions as are described in the literature by condensing an appropriate ortho-disubstituted benzene with a two-carbon synthon.

The compounds of formula (I) wherein Z is a radical (a-1) and $R^1$ is hydrogen, $C_{1-6}$alkyl or $Ar^2$, said compound being represented by formula (I-a-1-a), may be obtained by condensing an appropriate ortho-benzenediamine of formula (VIII-a) with a 1,2-diketone of formula (IX).

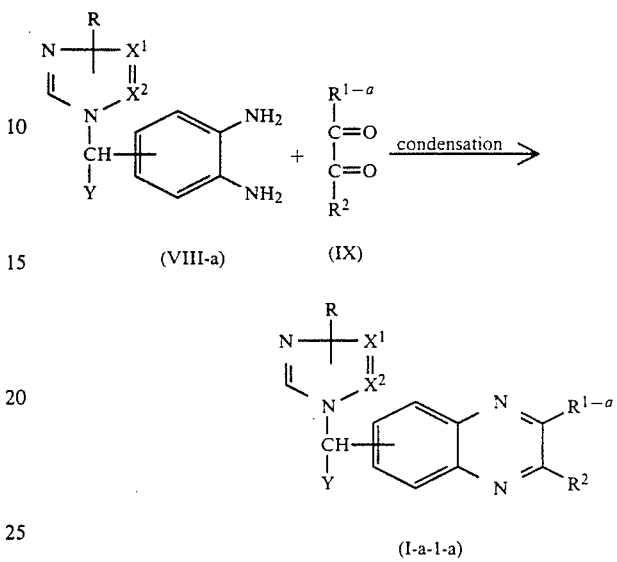

In (IX) and (I-a-1-a) $R^{1-a}$ represents hydrogen, $C_{1-6}$alkyl or $Ar^2$.

The condensation of the (1H-azol-1-ylmethyl) substituted ortho-diamine of formula (VIII-a) and the 1,2-diketone of formula (IX) can be carried out by mixing the reactants in a suitable solvent such as, for example, an alkanol, e.g. methanol, ethanol, propanol and the like; an ether, e.g. tetrahydrofuran, 1,4-dioxane, 1,1'-oxybisbutane and the like; a halogenated hydrocarbon, e.g. trichloromethane, dichloromethane and the like; a dipolar aprotic solvent, e.g., N,N-dimethylformamide, N,N-dimethylacetamide, dimethylsulfoxide; an aromatic hydrocarbon, e.g. benzene, methylbenzene, dimethylbenzene and the like or mixtures of such solvents optionally in the presence of a carboxylic acid, e.g. acetic acid and the like, a mineral acid such as, for example hydrochloric acid, sulfuric acid, or a sulfonic acid such as, for example, methanesulfonic acid, benzenesulfonic acid, 4-methylbenzenesulfonic acid and the like. Somewhat elevated temperatures may be appropriate to enhance the rate of the reaction and in some cases the reaction may even be carried out at the reflux temperature of the reaction mixture. The water which is liberated during the condensation may be removed from the mixture by azeotropical distillation, distillation and the like methods. As suitable 1,2-diketones of formula (IX) there may be named for example, ethanedial, diphenylethanedione, 2,3-butanedial and the like two carbon synthons.

The compounds of formula (I) wherein Z is a radical of formula (a-2) and n is 0, said compounds being represented by (I-a-2-a), may be obtained by condensing an appropriate ortho-benzenediamine of formula (VIII-b) with an appropriate α-keto acid of formula (X) or a functional derivative thereof such as, for example, an ester, a halide and the like.

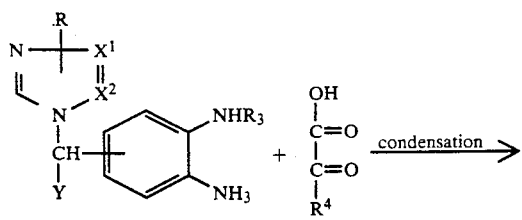

(VIII-b)   (X)

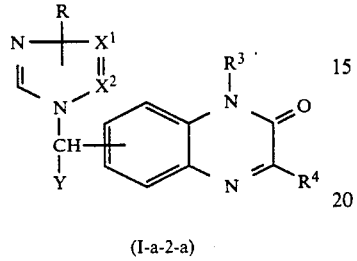

(I-a-2-a)

The condensation of the (1H-azol-1-ylmethyl) substituted ortho-diamine of formula (VIII-b) and the α-keto acid or ester of formula (X) can be carried out by mixing the reactants in a suitable solvent such as, for example, water, an alkanol, e.g. methanol, ethanol, propanol and the like; an ether, e.g. tetrahydrofuran, 1,4-dioxane, 1,1'-oxybisbutane and the like; a halogenated hydrocarbon, e.g. trichloromethane, dichloromethane and the like; a dipolar aprotic solvent, e.g. N,N-dimethylformamide, N,N-dimethylacetamide, dimethylsulfoxide, and the like; an aromatic hydrocarbon, e.g. benzene, methylbenzene, dimethylbenzene and the like; and mixtures of such solvents optionally in the presence of a carboxylic acid, e.g. acetic acid and the like, a mineral acid such as, for example hydrochloric acid, sulfuric acid, or a sulfonic acid such as, for example, methanesulfonic acid, benzenesulfonic acid, 4-methylbenzenesulfonic acid and the like. Somewhat elevated temperatures may be appropriate to enhance the rate of the reaction and in some cases the reaction may even be carried out at the reflux temperature of the mixture. The water which is liberated during the condensation may be removed from the mixture by azeotropical distillation, distillation and the like methods. As representative α-keto acids of formula (X) there may be named 2-oxopentanoic acid, 2-oxoacetic acid, 2-oxopropanoic acid and the like acids. As suitable α-keto esters there may be named for example, ethyl 2-oxopropanoate, ethyl 4-methyl-2-oxopentanoate, ethyl 3-methyl-2-oxobutanoate, methyl β-oxobenzeneacetate, diethyl 2-methyl-3-oxo-1,4-butanedioate, diethyl-1,3-propanedioate and the like esters. As suitable halides there may be named 2-oxopropanoyl chloride, dichloroacetyl chloride, diethoxyacetyl chloride.

In some instances the reaction of (VIII-b) with (X) first yields an intermediate of formula (XI-a) which may in situ or, if desired, after isolating and purifying it, be cyclized by heating it in the presence of an acid such as, for example, a carboxylic acid, e.g. acetic acid and the like, a mineral acid such as, for example hydrochloric acid, sulfuric acid, or a sulfonic acid such as, for example, methanesulfonic acid, benzenesulfonic acid, 4-methylbenzenesulfonic acid and the like.

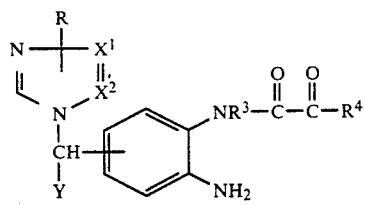

(XI-a)

Alternatively compounds of formula (I-a-2-a) may be prepared by the reduction of an intermediate of formula (XI-b).

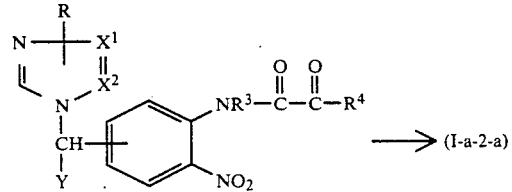

(XI-b)

The reduction and cyclization of (XI-b) can conveniently be conducted by stirring the starting compound in a reaction inert solvent such as, for example, an alkanol, e.g. methanol, ethanol, propanol and the like, as ester, e.g. ethyl acetate, butylacetate and the like, an aromatic hydrocarbon, e.g. benzene, methylbenzene and the like; a halogenated hydrocarbon, e.g. chloromethane in the presence of hydrogen and an appropriate metal catalyst such as, for example, palladium-on-charcoal, Raney nickel and the like, optionally at an elevated temperature and/or pressure.

The compounds of formula (I) wherein Z is a radical of formula (a-2) wherein n is 1, said compounds being represented by formula (I-a-2-b) may be prepared by cyclizing an ortho-nitroanilide containing a suitable activated methylenegroup of formula (XII-a).

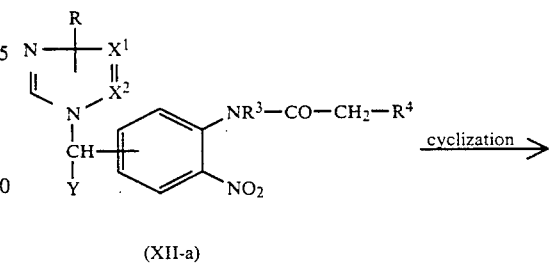

(XII-a)

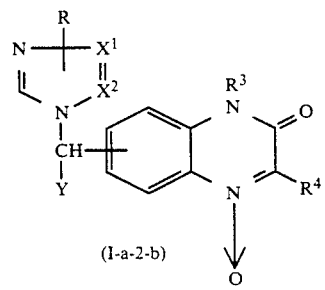

(I-a-2-b)

The base promoted cyclization of (XII-a) can be conducted according to art-known cyclizing procedures as described in, for example, J. Chem. Soc., 1963, 2429; J.

Med. Soc., 1966, 2285 and J. Org. Chem., 1968, 30, 201 by stirring, and optionally heating the ortho-nitroanilide (XII-a) in a suitable solvent such as, for example water, an alcohol, e.g. methanol, ethanol and the like; a polar aprotic solvent, e.g. pyridine and the like; a ketone, e.g. propanone and the like; an aromatic hydrocarbon e.g. benzene, dimethylbenzene and the like; a halogenated hydrocarbon, e.g. trichloromethane, tetrachloromethane and the like; an ether, e.g. tetrahydrofuran or a mixture of such solvents, in the presence of an appropriate base. Suitable bases are for example, an alkaline metal or an earth alkaline metal carbonate, hydrogen carbonate, hydroxide or hydride, e.g. sodium carbonate, sodium hydrogen carbonate, potassium carbonate, sodium hydroxide, sodium hydride and the like, or an organic base such as, for example, a tertiary amine, e.g. N-(1-methylethyl)-2-propanamine and the like. Depending on the reaction conditions and the nature of the activating group $R^4$, the obtained 3-substituted quinoxaline-N-oxide of formula (I-a-2-b) may be decomposed to give the corresponding unsubstituted N-oxide wherein $R^4$ is hydrogen.

The compounds of formula (I-a-2-b) can also be prepared by cyclizing an ortho anilide of formula (XII-b).

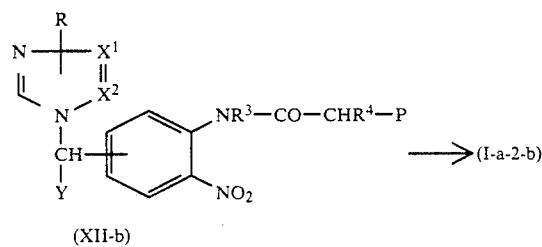

(XII-b)

In (XII-b) P represents a suitable activating group such as, for example, $C_{1-4}$alkylcarbonyl, arylcarbonyl and the like. The base promoted cyclization of (XII-b) can be carried out according similar procedures as described hereinabove for the cyclization of (XII-a). Similar cyclization procedures are also outlined in J. Chem. Soc. 1963, p. 2431 and J. Chem. Soc. 1964, p. 2666.

The quinoxaline-2,3-diones of formula (I-a-3) can be prepared by condensing an intermediate of formula (VIII-c) with oxalic acid (XIII) or a functional derivative thereof such as, for example an ester or halide.

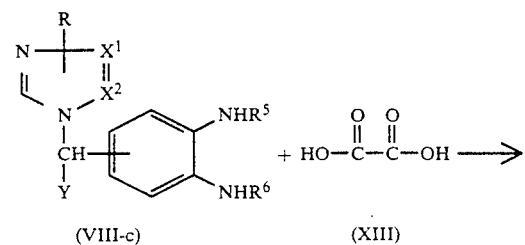

(VIII-c)     (XIII)

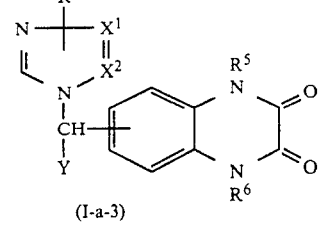

(I-a-3)

The condensation of (VIII-c) and (XIII) is conveniently carried out by mixing the reactants, optionally in a reaction inert solvent such as, for example, water; an alkanol, e.g. methanol, ethanol and the like; a halogenated hydrocarbon, e.g. trichloromethane, dichloromethane and the like; an ether, e.g. tetrahydrofuran; a dipolar aprotic solvent, e.g. N,N-dimethylformamide, N,N-dimethylacetamide, dimethylsulfoxide, an aromatic hydrocarbon, e.g. benzene, methylbenzene, dimethylbenzene and the like; an ester, e.g. ethyl acetate or a mixture of such solvents optionally in the presence of a carboxylic acid, e.g. acetic acid and the like, a mineral acid such as, for example hydrochloric acid, sulfuric acid, or a sulfonic acid such as, for example, methanesulfonic acid, benzenesulfonic acid, 4-methylbenzenesulfonic acid and the like. In some instances the reaction may even be carried out in an excess of carboxylic acid, e.g. acetic acid and the like. Somewhat elevated temperatures may be appropriate to enhance the reaction and in some cases the reaction may even be carried out at the reflux temperature of the mixture. The water or acid which is liberated during condensation may be removed by azeotropical distillation, distillation, complexation, salt formation and the like methods.

The compounds of formula (I) wherein Z is a radical of formula (a-4) may be prepared by condensation of an ortho diamine of formula (VIII-d) with an α-halo acid of formula (XIV) or the ester form thereof

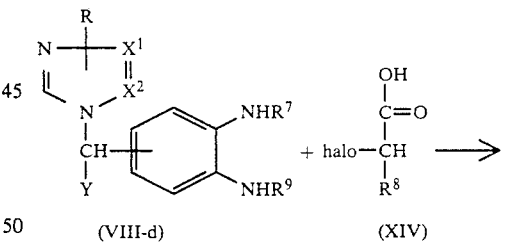

(VIII-d)     (XIV)

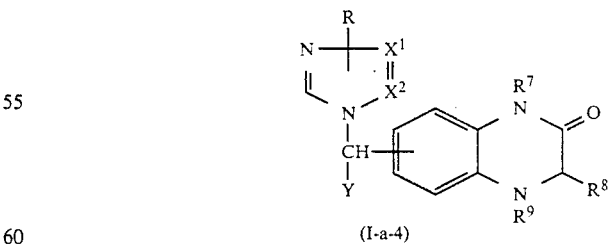

(I-a-4)

The above mentioned condensation can be carried out by stirring the reactants at an enhanced temperature in a suitable solvent such as, for example, water; an alkanol, e.g. methanol, ethanol, propanol and the like; an ether, e.g. 1,4-dioxane, 1,1'-oxybisethane, tetrahydrofuran and the like; an ester, e.g. ethylacetate and the like; a halogenated hydrocarbon, e.g. trichloromethane, tetrachloromethane and the like; a dipolar aprotic solvent, e.g. N,N-dimethylformamide, N,N-dimethylacetamide, dimethylsulfoxide and the like, an aromatic hydrocarbon, e.g. benzene, methylbenzene, dimethylbenzene and the like; a ketone, e.g. 2-propanone, 4-methyl-2-pentanone and the like and mixtures of such solvents. The addition of an appropriate base such as, for example, an alkali metal carbonate, hydrogen carbonate or hydroxide, e.g. sodium carbonate, sodium hydrogen carbonate, ammonium hydroxide or an organic base such as, for example, N,N-diethylethanamine and the like, may be utilized to pick up the acid which is liberated during the course of the reaction.

Alternatively the α-ketotetrahydroquinoxalines of formula (I-a-4) wherein $R^7$ is hydrogen, said compounds being represented by (I-a-4-a) may be prepared by the reduction of an appropriately substituted ortho-nitrophenylglycine of formula (XV).

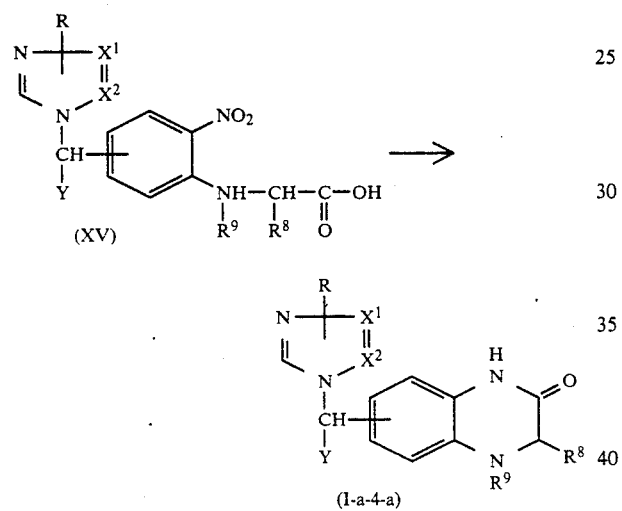

The reduction of the ortho-nitrophenylglycine of formula (XV) can conveniently be conducted by stirring the starting material in a reaction-inert solvent such as, for example, an alkanol, e.g. methanol, ethanol, propanol and the like, an ester, e.g. ethyl acetate, butylacetate and the like, an aromatic hydrocarbon, e.g. benzene, methylbenzene and the like; a halogenated hydrocarbon, e.g. chloromethane in the presence of hydrogen and an appropriate metal catalyst such as, for example, palladium-on-charcoal, Raney nickel and the like, optionally at an elevated temperature and/or pressure. Alternatively the reduction may be carried out with sodium dithionite in the presence of acetic acid or in aqueous alkanol, e.g. an aqueous ethanol solution.

Alternatively, some compounds of formula (I) may also be prepared according to procedures analogous to those described in the literature for the preparation of azoles by cyclizing an appropriate starting material.

The compounds of formula (I-x) may also be prepared, for example, by cyclizing an intermediate of formula (XVI) and desulfurating the thus obtained intermediate of formula (XVII).

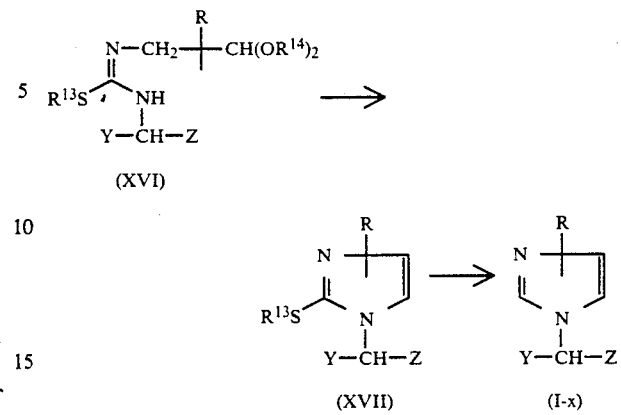

In formulae (XVI) and (XVII) $R^{13}$ represents hydrogen or $C_{1-6}$alkyl and $R^{14}$ represents $C_{1-6}$alkyl or both $R^{14}$ taken together form a $C_{2-3}$alkanediyl radical.

Said cyclization reaction may conveniently be conducted by stirring and heating intermediate (XVI) in an aqueous acidic solvent, e.g. in aqueous hydrochloric or in concentrated sulfuric acid. The intermediate (XVII) may be desulfurated following art-known procedures, e.g., by treatment with Raney nickel in the presence of an alkanol, e.g. methanol, ethanol and the like, or by treatment with nitric acid, optionally in the presence of sodium nitrite.

The compounds of formula (I-y) may be prepared from a hydrazine derivative of formula (XVIII) by reaction with s-triazine following the procedures described in J. Org. Chem., 1956, 1037.

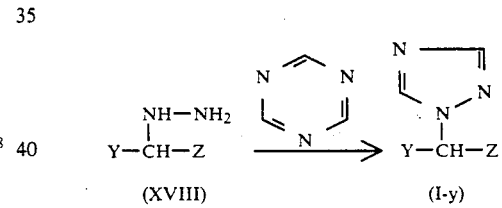

The intermediate hydrazine (XVIII) and the corresponding intermediate amine of formula Y—CH(NH-2)—Z (XIX) may also advantageously be converted into azoles, wherein —$X^1$=$X^2$— is a bivalent radical of formula (x), (y) or (z), following the procedures described in U.S. Pat. No. 4,267,179, incorporated herein by reference.

The compounds of formula (I) can also be converted into each other following art-known group transformation procedures. The deoxygenation of the N-oxide of formula (I-a-2) can be carried out by stirring and, if desired, heating the starting compounds in a suitable solvent in the presence of hydrogen or hydrazine and an appropriate metal catalyst such as, for example, Raney nickel, Raney cobalt, platinum-on-charcoal, palladium-on-charcoal and the like metal catalysts. Suitable solvents are water, an alkanol, e.g. methanol, ethanol and the like, an ether, e.g. tetrahydrofuran and the like, and mixtures of such solvents whereto an appropriate base has been added such as, for example, an alkali metal carbonate, hydrogen carbonate or hydroxide, e.g. sodium carbonate, sodium hydrogen carbonate, sodium hydroxide and the like. Alternatively the deoxygenation of the N-oxide of formula (I-a-2-b) may be carried out with sodium dithionite in the presence of acetic acid or in an aqueous alkanol, e.g. an aqueous ethanol solution. It further proved possible to accomplish the deoxygenation by stirring the N-oxide in the presence of zinc and acetic acid.

The α-ketotetrahydroquinoxalines of formula (I-a-4) may also be converted to a quinoxaline of formula (I-a-2) according to art-known dehydrogenation procedures as described for example J. Chem. Soc., 1953, 2816. For example, the dehydrogenation of the compounds of formula (I-a-4) can be carried out by heating the starting compound in an aqueous alkaline solution optionally in the presence of an appropriate oxidant such as, for example, peroxide, silver nitrate or manganese (IV) oxide.

Compounds of formula (I-a-2) wherein $R^3$ is hydrogen and n is 0 may also be converted into the corresponding compounds of formula (I-a-1) wherein $R^1$ is halo by treatment with a halogenating agent such as, for example, thionyl chloride, phosphoryl chloride, pentachloro phosphorane, sulfuryl chloride and the like. The thus obtained compounds wherein $R^1$ is halo may further be converted into quinoxalines of formula (I-a-1) wherein $R^1$ is $C_{1-6}$alkyloxy or mono or di($C_{1-6}$alkyl)amino by reacting the starting compounds with an appropriate amine or alcohol, preferably an alkali metal or earth alkaline metal salt of said alcohol. Some compounds of formula (I) may also be N-alkylated or N-aminated according to art known procedures.

Compounds of formula (I-a-5) can be obtained by reducing the corresponding compounds of formula (I-a-1) with an appropriate reducing agent such as, for example, an alkali metal borohydride, e.g. lithium, potassium or preferably, sodium borohydride, sodium cyanoborohydride and the like reducing agents in a reaction inert solvent.

A number of intermediates and starting materials in the foregoing preparations are known compounds which may be prepared according to art-known methodologies of preparing said or similar compounds and some intermediates are new. A number of such preparation methods will be described hereinafter in more detail.

Intermediates of formula (III), (V) and (VII) wherein Y is other than hydrogen can be prepared from an appropriately substituted quinoxaline derivative of formula (XX) according to the following reaction sequence.

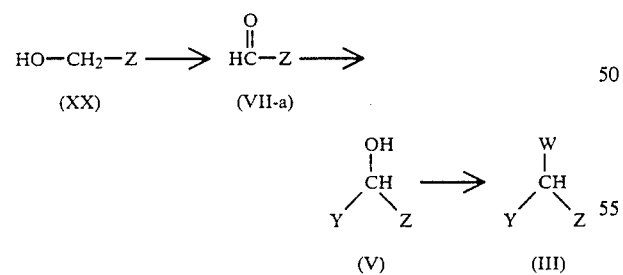

The hydroxymethyl moiety of formula (XX) is converted into a formyl moiety with a suitable oxidizing agent, e.g. manganese (IV) oxide or potassium permanganate, and subsequently reacted with a metal alkyl, e.g. methyllithium, butyllithium, metal aryl, e.g. phenyllithium, or with a complex metal alkyl or aryl in a suitable solvent such as, for example, an ether, e.g. tetrahydrofuran, 1,1'-oxybisethane and the like to form the secundary alcohols. The desired intermediates of formula (III) may then be obtained by converting the alcohol function of the intermediate of formula (V) into an appropriate leaving group W following standard procedures as known in the art. For example, halides are generally prepared by the reaction of (V) with an appropriate halogenating agent such as, for example, thionyl chloride, sulfuryl chloride, pentachlorophosphorane, pentabromophosphorane, phosphorylchloride, hydrochloric acid, hydrobromic acid and the like halogenating agents. The intermediates of formula (III) wherein Y is hydrogen can be obtained directly from the intermediates of formula (VII) following the procedure described hereinabove for converting (V) into (III).

Some intermediates of formula (III) wherein Y is other than hydrogen may also be prepared by acylating an intermediate quinoxaline derivative of formula (XXI) with an appropriate acylating reagent (XXII) according to art-known Friedel-Crafts acylation reaction procedures, reducing the obtained ketone (VII-b) with an appropriate reductant, e.g. sodium borohydride and the like in a suitable solvent such as an alcohol, e.g. methanol, ethanol; water or mixtures thereof with tetrahydrofuran and subsequently converting the alcohol function into an appropriate leaving group W as described hereinbefore.

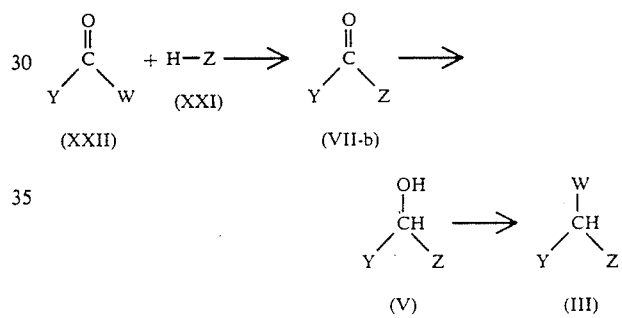

Some intermediates of formula (III) may also be prepared by cyclizing an appropriate benzaldehyde or ketone derivative of the general formula (XXIII) according to similar cyclization procedures as described hereinabove for the synthesis of the compounds of formula (I-a-1), (I-a-2), (I-a-3), (I-a-4) or (I-a-5), reducing the thus obtained quinoxaline with an appropriate reductant, e.g. sodium borohydride, sodium cyanoborohydride and the like reagents and subsequently converting the alcohol function of (V) in an appropriate leaving group. Depending on the cyclization procedures it may be appropriate to protect the aldehyde or ketone function according to art-known procedures.

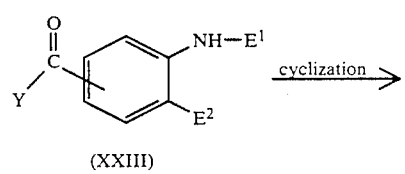

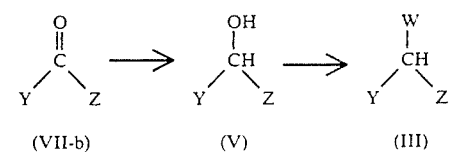

In (XXIII) the meanings of $E^1$ and $E^2$ are selected in such a manner to enable a cyclization reaction. For example, as appropriate intermediates of formula (XXIII) there may be named the following:

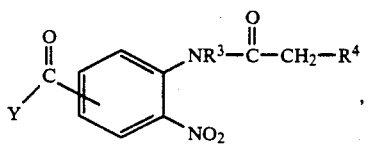

(XXIII-a)

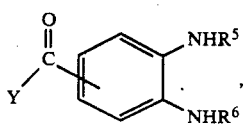

(XXIII-b)

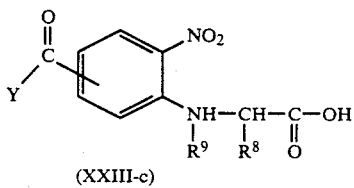

(XXIII-c)

More particular intermediates to prepare quinoxaline compounds may be prepared according the following procedures. The intermediates of formula (XI-b), (XII-a) and (XII-b) can conveniently be prepared by reacting an intermediate (XXV) with a carboxylic acid of formula (XXIV-a), (XXIV-b) or (XXIV-c) or a functional derivative thereof.

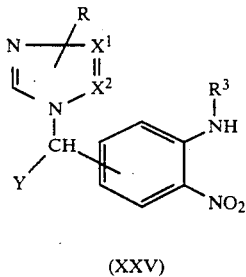

(XXV)

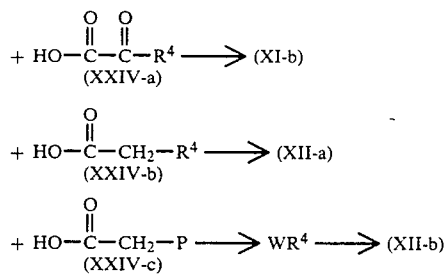

Said functional derivative of (XXIV-a), (XXIV-b) or (XXIV-c) are meant to comprise the halide, a symmetrical or mixed anhydride, amide and ester forms of (XXIV-a), (XXIV-b) or (XXIV-c). In the instance where $R^4$ represents a $C_{1-4}$alkylcarbonyl group in formula (XXIV-b) the hydroxyl group taken together with $R^4$ may also form a reactive lactone such as, for example, 4-methylene-2-oxetanone. Functional derivatives may be prepared following art-known procedures, for example, by reacting the carboxylic acid of formula (XXIV) with thionyl chloride, phosphorous trichloride, polyphosphoric acid, phosphoryl chloride and the like, or by reacting the carboxylic acid of formula (XXIV) with an acyl halide, e.g. acetyl chloride, ethyl carbonochloridate and the like. Or the intermediates (XXV) and (XXIV) may be coupled in the presence of a suitable reagent capable of forming amides, e.g. dicyclohexylcarbodiimide, 1,1'-biscarbonyl[1H-imidazole], 2-chloro-1-methylpyridinium iodide and the like.

Said amidation reactions may conveniently be carried out by stirring the reactants in a suitable reaction-inert solvent, such as, for example, a halogenated hydrocarbon, e.g. dichloromethane, trichloromethane and the like, an aromatic hydrocarbon, e.g. methylbenzene and the like, an ether, e.g. 1,1'-oxybisethane, tetrahydrofuran and the like or a dipolar aprotic solvent, e.g. N,N-dimethylformamide, N,N-dimethylacetamide and the like. The addition of a suitable base may be appropriate, in particular a tertiary amine such as, N,N-diethylethanamine. The water, the alcohol or the acid which is liberated during the course of the reaction may be removed from the reaction mixture according methodologies generally known in the art such as, for example, azeotropical distillation, complexation and salt formation.

Intermediates of formula (VIII) and (XXV) can easily be prepared according to procedures described in U.S. Pat. No. 4,859,684 corresponding to EP-A-260,744 and U.S. Ser. No. 223,486 corresponding to EP-A-0,293,278 incorporated herein by reference for the process of preparing the intermediates of formula (VIII) and (XXV).

The intermediates of formula (XVI) can be prepared from an amine of formula (XXVII) by reaction with a reagent of formula (XXVI) and optionally S-alkylating the thus obtained thiourea with a $C_{1-6}$alkylhalide.

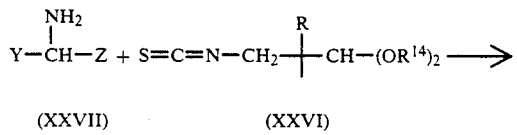

(XXVII)        (XXVI)

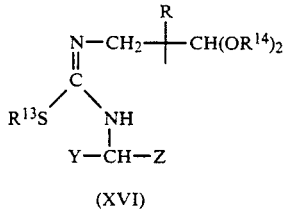

(XVI)

The compounds of formula (I) and some of the intermediates in this invention have an asymmetric carbon atom in their structure. This chiral center may be present in a R- and a S-configuration, this R- and S-notation being in correspondence with the rules described in Pure Appl. Chem., 1976, 45, 11-30. Pure stereochemically isomeric forms of the compounds of this invention may be obtained by the application of art-known procedures. Diastereoisomers may be separated by physical separation methods such as selective crystallization and chromatographic techniques, e.g. counter current distribution, and enantiomers may be separated from each other by the selective crystallization of their diastereomeric salts with optically active acids. Pure stereochemically isomeric forms may also be derived from the corresponding pure stereochemically isomeric forms of the appropriate starting materials, provided that the reaction occurs stereospecifically.

The compounds of the present invention, their pharmaceutically acceptable acid addition salts and their possible stereochemically isomeric forms have useful pharmacological properties. For example, they suppress the plasma elimination of retinoids, such as, alltrans-retinoic acid, 13-cis retinoic acid and their derivatives. The latter results in more sustained/higher tissue concentrations of retinoic acid and improved control of the differentiation and growth of various cell types. In addition some compounds inhibit the formation of androgens from progestines and/or inhibit the action of the enzyme complex aromatase which catalyses the formation of estrogens from androgenic steroids in mammals. A number of compounds also show an inhibitory action on the biosynthesis of thromboxane $A_2$.

Said property of the compounds of the invention to delay the metabolism of retinoic acid can easily be evidenced in various in vivo experiments. A particular test procedure is described hereinafter as the "Metabolism of endogenous or exogenously administered all-trans-retinoic acid" test and demonstrates the suppression of the plasma elimination of endogenous or exogenously administered all-trans-retinoic acid. As such, the compounds of formula (I) can be used to control the rate of growth and differentiation of various cell types which effects are known to be affected by retinoids. The ability of retinoids, such as, 13-cis-retinoic acid, all-trans-retinoic acid and their derivatives to modulate differentiation and proliferation in several cell types whether they are of epithelial or mesenchymal origin is extensively studied and reviewed in J. Clin. Chem. Clin, Biochem., 26, 479-488 (1983); Pharmacological Reviews 36, 935-1005, (1984), Arch. Dermatol. 117, 160-180; (1981) and Journal of Medicinal Chemistry 25, 1269-1277, (1982).

In view of their capability to delay the metabolism of retinoic acid the compounds can thus be used in the treatment of disorders which are characterized by an increased proliferation and/or abnormal differentiation of epithelial cells. In particular the compounds of the invention can be used for treatment of carcinoma which is essentially a derailment of cellular differentiation, occurring in epithelial tissues. Other uses include, in addition to cancer treatment, the treatment of a variety of disorders of keratinization such as, for example, acne, psoriasis, lamellar ichthyosis, plantar warts, callosities, acanthosis nigricans, lichen planus, molluscum, melasma, corneal epithelial abrasion, geographic tongue, Fox-Fordyce disease, cutaneous metastatic melanoma and keloids, epidermolytic hyperkeratosis, Darier's disease, pityriasis rubra pilaris, congenital ichthyosiform erythroderma, hyperkeratosis palmaris et plantaris, and similar diseases.

The anti-tumor activity may be demonstrated in several retinoic acid-sensitive and insensitive cell lines and solid tumors such as, for example, in Ta3-Ha induced mamma tumors in female mice.

The inhibition of androgen and/or estrogen formation can be demonstrated by analyzing the effects of the compounds of the invention on the conversion of progestins into androgens in the presence of testicular microsomes or on the conversion of androstenedione into estrone and estradiol in the presence of human placental microsomes. The in vivo-inhibition of androgen or estrogen formation can, for example, be demonstrated by measuring the suppression of the plasma testosterone or estrogen concentration in dogs, rats or mice. A number of relevant tests have been described in EP-A-260,744 and EP-A-293,978 (U.S. Pat. No. 4,943,574), both incorporated herein by reference. In view of their capability to inhibit the biosynthesis of estrogens and/or androgens the compounds can be used in the treatment of estrogen or androgen dependent disorders such as, for example, breast cancer, endometriosis, endometrial cancer, polycystic ovarian disease, benign breast disease, prostatic cancer and hirsutism.

The beneficial effect of androgen inhibitors in these disorders, especially in the treatment of prostatic cancer, is described in, e.g., Journal of Urology 132, 61-63 (1984). The beneficial effect of aromatase inhibitors in these disorders, especially in the treatment of breast cancer, is described in, e.g. Cancer Research, 42, Suppl. 8:3261s (1982).

In view of the usefulness of the subject compounds it is evident that the present invention provides a method for treating mammals suffering from disorders which are characterized by an increased proliferation and/or abnormal differentiation of normal, preneoplastic or neoplastic cells, whether they are epithelial or mesenchymal; whether they are of ectodermal, endodermal or mesodermal origin; or whether they are estrogen dependent, androgen dependent or nonestrogen and nonandrogen dependent. Said method comprises the systemic or topical administration to the latter of an amount, effective to treat said disorders, of a compound of formula (I), a pharmaceutically acceptable acid-addition salt, or a possible stereochemically isomeric form thereof. In particular the present invention provides a method in which the growth and differentiation in said normal, preneoplastic and neoplastic cells is sensitive to the actions of retinoids.

Those of skill in treating disorders which are characterized by an excessive proliferation and/or abnormal differentiation of tissues could determine the effective amount from the test results presented hereinafter. In general it is contemplated than an effective amount would be from 0.001 mg/kg to 50 mg/kg body weight and more preferably from 0.01 mg/kg to 10 mg/kg body weight.

The subject compounds may be formulated into various pharmaceutical forms for administration purposes. As appropriate compositions there may be cited all compositions usually employed for systemically or topically administering drugs. To prepare the pharmaceutical compositions of this invention, an effective amount of the particular compound, optionally in acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represents the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. As appropriate compositions for topical application there may be cited all compositions usually employed for topically administering drugs, e.g., creams, gellies, dressings, shampoos, tinctures, pastes, ointments, salves, powders and the like. Application of said compositions may be by aerosol e.g. with a propellent such as nitrogen carbon dioxide, a freon, or without a propellent such as a pump spray, drops, lotions, or a semisolid such as a thickened composition which can be applied by a swab. In particular compositions, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discreate units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powders packets, wafers, injectable solutions or suspensions, teaspoonfuls, tablespoonfuls and the like, and segregated multiples thereof.

Other such compositions are preparations of the cosmetic type, such as toilet waters, packs, lotions, skin milks or milky lotions. Said preparations contain, besides the active ingredient, components usually employed in such preparations. Examples of such components are oils, fats, waxes, surfactants, humectants, thickening agents, antioxidants, viscosity stabilizers, chelating agents, buffers, preservatives, perfumes, dyestuffs, lower alkanols, and the like. If desired, further ingredients may be incorporated in the compositions, e.g. antiinflammatory agents, antibacterials, antifungals, disinfectants, vitamins, sunscreens, antibiotics, or other anti-acne agents. Examples of oils comprise fats and oils such as olive oil and hydrogenated oils; waxes such as beeswax and lanolin; hydrocarbons such as liquid paraffin, ceresin, and squalane; fatty acids such as stearic acid and oleic acid; alcohols such as cetyl alcohol, stearyl alcohol, lanolin alcohol, and hexadecanol; and esters such as isopropyl myristate, isopropyl palmitate and butyl stearate. As examples of surfactants there may be cited anionic surfactants such as sodium stearate, sodium cetylsulfate, polyoxyethylene lauryl-ether phosphate, sodium N-acyl glutamate; cationic surfactants such as stearyldimethyl-benzylammonium chloride and stearyltrimethylammonium chloride; ampholytic surfactants such as alkylaminoethylglycine hydrochloride solutions and lecithin; and nonionic surfactants such as glycerin monostearate, sorbitan monostearate, sucrose fatty acid esters, propylene glycol monostearate, polyoxyethylene oleylether, polyethylene glycol monostearate, polyoxyethylene sorbitan monopalmitate, polyoxyethylene coconut fatty acid monoethanolamide, polyoxyethylene polyoxypropylene glycol (e.g. the materials sold under the trademark "Pluronic"), polyoxyethylene castor oil, and polyoxyethylene lanolin. Examples of humectants include glycerin, 1,3-butylene glycol, and propylene glycol; examples of lower alcohols include ethanol and isopropanol; examples of thickening agents include xanthan gum, hydroxypropyl cellulose, hydroxypropyl methyl cellulose, polyethylene glycol and sodium carboxymethyl cellulose; examples of antioxidants comprise butylated hydroxytoluene, butylated hydroxyanisole, propyl gallate, citric acid and ethoxyquin; examples of chelating agents include disodium edetate and ethanehydroxy diphosphate; examples of buffers comprise citric acid, sodium citrate, boric acid, borax, and disodium hydrogen phosphate; and examples of preservatives are methyl parahydroxybenzoate, ethyl parahydroxybenzoate, dehydroacetic acid, salicylic acid and benzoic acid. For preparing ointments, creams, toilet waters, skin milks, and the like, typically from 0.01 to 10% in particular from 0.1 to 5% and more in particular from 0.2 to 2.5% of the active ingredient will be incorporated in said compositions. In ointments or creams, the carrier for example consists of 1 to 20%, in particular 5 to 15% of a humectant, 0.1 to 10% in particular from 0.5 to 5% of a thickener and water; or said carrier may consist of 70 to 99%, in particular 20 to 95% of a surfactant, and 0 to 20%, in particular 2.5 to 15% of a fat; or 80 to 99.9% in particular 90 to 99% of a thickener; or 5 to 15% of a surfactant, 2–15% of a humectant, 0 to 80% of an oil, very small (<2%) amounts of preservative, colouring agent and/or perfume, and water. In a toilet water, the carrier for example consists of 2 to 10% of a lower alcohol, 0.1 to 10% or in particular 0.5 to 1% of a surfactant, 1 to 20%, in particular 3 to 7% of a humectant, 0 to 5% of a buffer, water and small amounts (<2%) of preservative, dyestuff and/or perfume. In a skin milk, the carrier typically consists of 10–50% of oil, 1 to 10% of surfactant, 50–80% of water and 0 to 3% of preservative and/or perfume. In the afore-mentioned preparations, all % symbols refer to weight by weight percentage. The humectant, surfactant, oil, etc... referred to in said preparations may be any such component used in the cosmetic arts but preferably will be one or more of the components mentioned hereinabove. Further, when in the above compositions one or more of the components make up the major part of the composition, the other ingredients can evidently be not present at their indicated maximum concentration and therefore will make up the remainder of the composition.

Particular compositions for use in the method of the present invention are those wherein the active ingredient is formulated in liposome-containing compositions. Liposomes are artificial vesicles formed by amphiphatic molecules such as polar lipids, for example, phosphatidyl cholines, ethanolamines and serines, sphingomyelins, cardiolipins, plasmalogens, phosphatidic acids and cerebiosides. Liposomes are formed when suitable amphiphathic molecules are allowed to swell in water or aqueous solutions to form liquid crystals usually of multilayer structure comprised of many bilayers separated from each other by aqueous material (also referred to as coarse liposomes). Another type of liposome known to be consisting of a single bilayer encapsulating aqueous material is referred to as a unilamellar vesicle. If water-soluble materials are included in the aqueous phase during the swelling of the lipids they become entrapped in the aqueous layer between the lipid bilayers.

In a further aspect of the invention there are provided particular pharmaceutical or cosmetical compositions which comprise an inert carrier, an effective amount of a compound of formula (I) an acid addition salt or a stereochemically isomeric form thereof and an effective amount of a retinoic acid, a derivative thereof or a stereochemically isomeric form thereof. Said retinoic acid containing compositions are particularly useful for treating acne or for retarding the effects of aging of the skin and generally improve the quality of the skin, particularly human facial skin. A pharmaceutical or cosmetical composition containing retinoic acid or a derivative thereof as the active ingredient in intimate admixture with a dermatologically acceptable carrier can be prepared according to conventional compounding techniques, such as those known for topical application of retinoic acid and its derivatives. Conventional pharmaceutical compounding techniques for topical application of retinoic acid are described for example in, U.S. Pat. Nos. 3,906,108 and 4,247,547, which are incorporated herein by reference. Preferred composition for topical application are in form of a cream, ointment or lotion comprising from 0.005 to 0.5% (particularly from 0.01 to 0.1%) alltrans-retinoic acid, 13-cis-retinoic acid or a derivative thereof and from 0.1 to 5% of a compound of formula (I) and, a dermatologically acceptable acid addition salt thereof or a stereochemically isomeric form thereof, in a semi-solid or liquid diluent or carrier. These preferred compositions should preferably be non-irritating and as far as possible they should be odorless and non-toxic. For convenience in applying to the skin, the composition usually contain, besides water or an organic solvent, several of certain organic emollients, emulsifiers for the aqueous and/or non aqueous phases of the compositions, wetting agents preservatives and agents that facilitate the penetration and remainence of the active agents in the skin.

The following examples are intended to illustrate and not to limit the scope of the present invention. Unless otherwise stated all parts therein are by weight.

EXPERIMENTAL PART

A. PREPARATION OF THE INTERMEDIATES

EXAMPLE 1

A mixture of 10 parts of 5-methylquinoxaline, 10 parts of 1,3-dibromo-5,5-dimethylimidazolidine-2,4-dione, 1.7 parts of benzenecarboperoxoic acid and 318 parts of tetrachloromethane was stirred for 16 hours at reflux temperature under 2 lamps of 250 Watt. The reaction mixture was cooled and the organic layer was decanted. The product was filtered off and dried, yielding 15.5 parts (100%) of 5-(bromomethyl)quinoxaline (interm. 1).

EXAMPLE 2

(a) To a stirred solution of 30 parts of (3,4-diaminophenyl) phenylmethanone in 240 parts of methanol were added 30 parts of an ethanedial solution in water 40%. The reaction mixture was stirred for 3 hours at reflux temperature. After cooling to room temperature, the precipitated product was filtered off, washed with methanol and dried, yielding 20 parts (59.3%) of phenyl (6-quinoxalinyl)methanone; mp. 120° C. (interm. 2).

(b) To a stirred and cooled (5° C.) solution of 20 parts of intermediate 2, namely phenyl (6-quinoxalinyl)methanone in 160 parts of methanol were added portionwise 3.2 parts of sodium tetrahydroborate. Upon completion, the reaction mixture was poured into water and the product was extracted with dichloromethane. The extract was washed with water, dried, filtered and evaporated to dry, yielding 20 parts (100%) of α-phenyl-6-quinoxalinemethanol as an oily residue (interm. 3).

(c) To a stirred and cooled (0° C.) mixture of 12 parts of intermediate 3, namely α-phenyl-6-quinoxalinemethanol, 213 parts of dichloromethane and 15.4 parts of N,N-diethylethanamine was added a solution of 8.8 parts of methanesulfonyl chloride in 26.6 parts of dichloromethane under nitrogen atmosphere. After stirring overnight at room temperature, the reaction mixture was evaporated, yielding 54 parts (100%) of α-phenyl-6-quinoxalinemethanol methanesulfonate (ester) as an oily residue (interm. 4).

EXAMPLE 3

(a) To a stirred mixture of 6.9 parts of 3,4-diaminobenzenemethanol, 1 part of N,N-diethylethanamine and 75 parts of water were added 2.9 parts of a solution of ethanedial in water 40% at about 55° C. The whole was stirred for 1 hour at 55°–60° C. The solvent was evaporated and the residue was purified by column chromatography over silica gel using a mixture of trichloromethane and methanol (95:5 by volume) as eluent. The pure fractions were collected and the eluent was evaporated. The residue was converted into the hydrochloride salt in 2-propanol and ethanol. The product was filtered off and dried, yielding 6.5 parts (66.1%) of 6-quinoxalinemethanol monohydrochloride; mp. >300° C. (interm. 5).

(b) To a stirred solution of 10 parts of intermediate 5, namely 6-quinoxalinemethanol in 133 parts of dichloromethane were added 20 parts of manganese(IV) oxide. After stirring for 3 hours at room temperature, the reaction mixture was filtered and the filtrate was evaporated, yielding 6.6 parts (67.3%) of 6-quinoxalinecarboxaldehyde; mp. 134° C. (interm. 6).

EXAMPLE 4

(a) To a stirred and refluxed Grignard complex previously prepared starting from 55.1 parts of 1-bromopropane, 10.9 parts of magnesium and tetrahydrofuran was added a solution of 25 parts of N-(4-formylphenyl)acetamide in 225 parts of dry tetrahydrofuran. After stirring for 1 hour at room temperature, the reaction mixture was poured into ice water and a saturated ammonium chloride solution. The organic layer was decanted (and set aside) and the remaining phase was extracted with ethyl acetate. The combined organic layers were dried, filtered and evaporated. The residue was purified by column chromatography over silica gel using a mixture of trichloromethane and methanol (98:2 by volume) as eluent. The pure fractions were collected and the eluent was evaporated, yielding 20 parts (64.3%) of N-[4-(1-hydroxybutyl)phenyl]acetamide as a residue (interm. 7).

(b) A mixture of 10 parts of intermediate 7, namely N-[4-(1-hydroxybutyl)phenyl]acetamide, 16.2 parts of 1,1'-carbonylbis[1H-imidazole] and 135 parts of tetrahydrofuran was stirred for 17 hours at room temperature. The reaction mixture was evaporated and the residue was taken up in trichloromethane. The organic phase was washed with a potassium carbonate solution 10% in water, dried, filtered and evaporated. The residue was purified by column chromatography (HPLC) over silica gel using a mixture of trichloromethane and methanol (95:5 by volume) as eluent. The pure fractions were collected and the eluent was evaporated, yielding 5.8 parts (45.0%) of N-[4-[1-(1H-imidazol-1-yl)butyl]-phenyl]acetamide; mp. 186° C. (interm. 8);

(c) To a stirred and cooled (0° C.) mixture of 2.57 parts of intermediate 8, namely N-[4-[1-(1H-imidazol-1-yl)butyl]phenyl]acetamide and 23.0 parts of concentrated sulfuric acid were added portionwise 1.01 parts of potassium nitrate. Upon complete addition, stirring was continued for 30 minutes at 0° C. The reaction mixture was poured into crushed ice and treated with ammonium hydroxide to pH 10. The product was extracted with trichloromethane. The extract was dried, filtered and evaporated, yielding 3 parts (99.4%) of N-[4-[1-(1H-imidazol-1-yl)butyl]-2-nitrophenyl]acetamide as a residue (interm. 9).

(d) A mixture of 11.5 parts of intermediate 9, namely N-[4-[1-(1H-imidazol-1-yl)butyl]-2-nitrophenyl]acetamide and 150 parts of a hydrochloric acid solution 3N was stirred for 3 hours at reflux temperature. The reaction mixture was poured into crushed ice and the whole was neutralized with concentrated ammonium hydroxide. The product was extracted with dichloromethane. The extract was dried, filtered and evaporated, yielding 8.8 parts (88.9%) of 4-[1-(1H-imidazol-1-yl)butyl]-2-nitrobenzenamine as a residue (interm. 10).

In a similar manner there were also prepared:
4-[1-(1H-imidazol-1-yl)propyl]-2-nitrobenzenamine as a residue (interm. 11);
4-[1-(1H-imidazol-1-yl)-3-methylbutyl]-2-nitrobenzenamine as a residue (interm. 12); and
4-[1-(1H-imidazol-1-yl)-2-methylpropyl]-2-nitrobenzenamine (interm. 13).

EXAMPLE 5

(a) To a stirred and cooled mixture (ice bath, 0° C.) of 30 parts of 1-(4-amino-3-nitrophenyl)-2-methyl-1-propanone and 390 parts of dichloromethane were added dropwise 33 parts of acetyl chloride. Upon complete addition, the reaction mixture was stirred for 12 hours at room temperature. The whole was poured into water and after the addition of sodium carbonate, stirring was continued for 15 minutes. The separated organic layer was dried, filtered and evaporated, yielding 36 parts (100%) of N-[4-(2-methyl-1-oxopropyl)-2-nitrophenyl]acetamide (interm. 14).

(b) To a stirred and cooled (ice water, 10° C.) solution of 30 parts of intermediate 14, namely N-[4-(2-methyl-1-oxopropyl)-2-nitrophenyl]acetamide in 240 parts of methanol were added portionwise 4.5 parts of sodium tetrahydroborate. Upon completion, stirring was continued for 1 hour. The reaction mixture was evaporated and the residue was extracted with dichloromethane (3×104 parts). The combined extracts were washed with water, dried, filtered and evaporated, yielding 32 parts (100%) of N-[4-(1-hydroxy-2-methylpropyl)-2-nitrophenyl]acetamide (interm. 15).

(c) To a stirred solution of 36 parts of intermediate 15, namely N-[4-(1-hydroxy-2-methylpropyl)-2-nitrophenyl]acetamide and 390 parts of dichloromethane were added 35.0 parts of N,N-diethylethanamine. After cooling to 0° C., 20.0 parts of methane-sulfonyl chloride were added dropwise to the previous mixture. Upon completion, stirring was continued for 12 hours at room temperature. The whole was poured into water and sodium carbonate was added while stirring. The product was extracted with dichloromethane. The extract was dried, filtered and evaporated, yielding 39 parts (100%) of N-[4-(1-chloro-2-methylpropyl)-2-nitrophenyl]acetamide (interm. 16).

(d) A mixture of 40 parts of intermediate 16, namely N-[4-(1-chloro-2-methylpropyl)-2-nitrophenyl]acetamide, 51 parts of 1H-1,2,4-triazole, 50 parts of potassium carbonate and 400 parts of acetonitrile was stirred for 2 hours at reflux temperature. After cooling, the whole was evaporated to dry and the residue was taken up in 300 parts of water. The product was extracted with dichloromethane. The extract was dried, filtered and evaporated. The residue was purified by column chromatography over silica gel using a mixture of dichloromethane and methanol (98:2 by volume) as eluent. The pure fractions were collected and the eluent was evaporated, yielding 22 parts (49.0%) of N-[4-[2-methyl-1-(1H-1,2,4-triazol-1-yl)propyl]-2-nitrophenyl]acetamide as an oil (interm. 17).

(e) A mixture of 20 parts of intermediate 17, namely N-[4-[2-methyl-1-(1H-1,2,4-triazol-1-yl)propyl]-2-nitrophenyl]acetamide and 200 parts of a hydrochloric acid solution 2N was stirred for 12 hours at room temperature. The reaction mixture was poured into 500 parts of water and the whole was neutralized with a concentrated potassium carbonate solution. The product was extracted with dichloromethane (3×130 parts). The combined extracts were dried, filtered and evaporated to dry. The residue was crystallized from 2,2'-oxybispropane, yielding 18.5 parts (97.7%) of 4-[2-methyl-1-(1H-1,2,4-triazol-1-yl)propyl]-2-nitrobenzenamine; mp. 206° C. (interm. 18).

In a similar manner there were also prepared:

TABLE 1

$$\begin{array}{c}\text{R}\\ \text{3N} \diagdown \text{X}^1\\ \text{2} \diagup \text{X}^2 \quad \text{NO}_2\\ \text{N}\\ \text{Y—CH} \diagdown \diagup \text{NH}_2\end{array}$$

| Int. No. | —X$^1$=X$^2$— | R | Y |
|---|---|---|---|
| 19 | —CH=N— | H | —C$_6$H$_5$ |
| 20 | —CH=CH— | 2-CH$_3$ | i-C$_3$H$_7$ |
| 21 | —CH=N— | H | C$_2$H$_5$ |
| 22 | —CH=N— | H | CH$_2$—CH(CH$_3$)$_2$ |
| 23 | —N=CH— | H | i-C$_3$H$_7$ |
| 24 | —CH=N— | H | C$_4$H$_9$ |
| 25 | —CH=N— | H | C$_3$H$_7$ |

EXAMPLE 6

(a) 1.61 Parts of sodium tetrahydroborate were added dropwise to a stirred solution of 11 parts of (4-amino-3-nitrophenyl) (2-fluorophenyl)methanone in 120 parts of methanol. Upon complete addition, stirring was continued for 1 hour at room temperature. The reaction mixture was poured into water and the product was extracted three times with 75 parts of trichloromethane. The combined extracts were dried, filtered and evaporated, yielding 11.3 parts (100%) of 4-amino-α-(2-fluorophenyl)-3-nitrobenzenemethanol as a residue (interm. 26).

(b) A mixture of 11.1 parts of intermediate 26, namely 4-amino-α-(2-fluorophenyl)-3-nitrobenzenemethanol, 13.7 parts of 1,1'-carbonylbis[1H-imidazole] and 90 parts of N,N-dimethylformamide was stirred for 12 hours at room temperature. After evaporation to dry, the residue was taken up in dichloromethane. The organic phase was washed with 50 parts of water, dried, filtered and evaporated. The residue was purified by column chromatography over silica gel using a mixture of dichloromethane and methanol (95:5 by volume) as eluent. The pure fractions were collected and the eluent was evaporated, yielding 6.5 parts (49.5%) of 4-[(2-fluorophenyl)(1H-imidazol-1-yl)methyl]-2-nitrobenzenamine; mp. 176° C. (interm. 27).

In a similar manner there were also prepared:

TABLE 2

| Int. No. | Y | physical data |
|---|---|---|
| 28 | 3-pyridinyl | 164.1° C. |
| 29 | phenyl | — |
| 30 | 2-thienyl | — |
| 31 | 4-fluorophenyl | 147.4° C. |
| 32 | 3-chlorophenyl | — |
| 33 | 3,4-dichlorophenyl | 152° C. |
| 34 | cyclopropyl | — |
| 35 | 4-methoxyphenyl | — |
| 36 | butyl | — |
| 37 | 3-fluorophenyl | — |
| 38 | 2-chlorophenyl | — |
| 39 | 4-methylphenyl | — |
| 40 | 3-CF$_3$-phenyl | — |
| 41 | 4-chlorophenyl | — |
| 42 | cyclohexyl | — |
| 43 | cyclopentyl | — |
| 44 | 4-[CH(CH$_3$)$_2$]-phenyl | — |

EXAMPLE 7

(a) To a stirred solution of 30 parts of 1-(4-chloro-3-nitrophenyl)-2-methyl-1-propanone in 240 parts of methanol was added a solution of 20 parts of methanamine in 160 parts of methanol. After stirring for 12 hours at 60° C., the reaction mixture was evaporated to dry, yielding 30 parts (100%) of 2-methyl-1-[4-(methylamino)-3-nitrophenyl]-1-propanone as a residue (interm. 45).

(b) To a stirred solution of 30 parts of intermediate 45, namely 2-methyl-1-[4-(methylamino)-3-nitrophenyl]-1-propanone in 320 parts of methanol were added dropwise 15 parts of sodium tetrahydroborate (the temperature was kept at 20° C.). Upon complete addition, stirring was continued for 30 minutes at room temperature. The reaction mixture was poured into water and the product was extracted with trichloromethane. The extract was dried, filtered and evaporated to dry, yielding 30 parts (100%) of 4-(methylamino)-α-(1-methylethyl)-3-nitrobenzenemethanol as an oily residue (interm. 46).

(c) To a stirred solution of 30 parts of intermediate 46, namely 4-(methylamino)-α-(1-methylethyl)-3-nitrobenzenemethanol in 270 parts of dry tetrahydrofuran were added 43.4 parts of 1,1'-carbonylbis[1H-imidazole]. After stirring for 24 hours at room temperature, the reaction mixture was evaporated to dry. The residue was taken up in trichloromethane and a potassium carbonate solution 10%. The separated organic layer was dried, filtered and evaporated to dry. The residue was purified by column chromatography over silica gel using a mixture of trichloromethane and methanol (99:1 by volume) as eluent. The pure fractions were collected and the eluent was evaporated, yielding 15 parts (40.9%) of 4-[1-(1H-imidazol-1-yl)-2-methylpropyl]-N-methyl-2-nitrobenzenamine as a residue (interm. 47).

EXAMPLE 8

To a stirred and cooled (0° C.) solution of 7 parts of 4-[1-(1H-imidazol-1-yl)propyl]-2-nitrobenzenamine in 126 parts of 1,2-dichloroethane were added 9.6 parts of 2-methylbenzeneacetyl chloride. After stirring for 12 hours at room temperature, the reaction mixture was poured into ice water and the product was extracted with dichloromethane. The extract was dried, filtered and evaporated in vacuo. The oily residue was purified by column chromatography over silica gel using a mixture of dichloromethane and methanol (98:2 by volume) as eluent. The eluent of the desired fraction was evaporated, yielding 9.6 parts (89.3%) of N-[4-[1-(1H-imidazol-1-yl)propyl]-2-nitrophenyl]-2-methylbenzeneacetamide; mp. 122° C. (interm. 48).

In a similar manner there were also prepared:

TABLE 3

| Int. No. | —X$^1$=X$^2$— | R | Y | Z | mp. |
|---|---|---|---|---|---|
| 49 | —CH=N— | H | C$_6$H$_5$ | C$_6$H$_5$ | — |
| 50 | —CH=CH— | H | i-C$_3$H$_7$ | 2-F—C$_6$H$_4$ | — |
| 51 | —CH=CH— | H | i-C$_3$H$_7$ | 4-CH$_3$—C$_6$H$_4$ | 114° C. |
| 52 | —CH=CH— | 2-CH$_3$ | i-C$_3$H$_7$ | C$_6$H$_5$ | — |
| 53 | —CH=CH— | H | i-C$_3$H$_7$ | 4-Br—C$_6$H$_4$ | — |
| 54 | —CH=CH— | H | i-C$_3$H$_7$ | 3,4-F$_2$—C$_6$H$_3$ | — |
| 55 | —CH=CH— | H | i-C$_3$H$_7$ | 4-OCH$_3$—C$_6$H$_4$ | — |

TABLE 3-continued

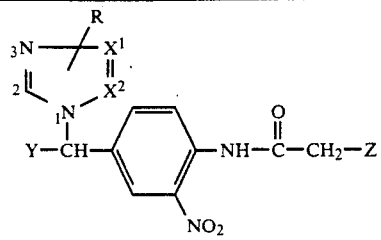

| Int. No. | —X$^1$=X$^2$— | R | Y | Z | mp. |
|---|---|---|---|---|---|
| 56 | —CH=CH— | H | 2,4-Cl$_2$—C$_6$H$_3$ | C$_6$H$_5$ | — |
| 57 | —CH=CH— | H | i-C$_3$H$_7$ | 3,4-(OCH$_3$)$_2$—C$_6$H$_3$ | — |
| 58 | —CH=CH— | H | i-C$_3$H$_7$ | 2,4-Cl$_2$—C$_6$H$_3$ | — |
| 59 | —CH=CH— | H | i-C$_3$H$_7$ | 2-naphthalenyl | 144° C. |
| 60 | —CH=CH— | H | i-C$_3$H$_7$ | 3,4,5-(OCH$_3$)$_3$—C$_6$H$_2$ | — |
| 61 | —CH=CH— | H | i-C$_3$H$_7$ | 2-thienyl | — |
| 62 | —CH=CH— | H | i-C$_3$H$_7$ | 2-OCH$_3$—C$_6$H$_4$ | — |
| 63 | —CH=CH— | H | i-C$_3$H$_7$ | 1-naphthalenyl | — |
| 64 | —CH=CH— | H | i-C$_3$H$_7$ | 2-Cl—C$_6$H$_4$ | — |
| 65 | —CH=CH— | H | i-C$_3$H$_7$ | 3-OH—C$_6$H$_4$ | — |
| 66 | —CH=CH— | H | i-C$_3$H$_7$ | 3-Br—C$_6$H$_4$ | — |
| 67 | —CH=CH— | H | i-C$_3$H$_7$ | 3-thienyl | — |
| 68 | —CH=N— | H | i-C$_3$H$_7$ | 2-thienyl | — |
| 69 | —CH=CH— | H | i-C$_3$H$_7$ | 2Cl,6F—C$_6$H$_3$ | — |
| 70 | —CH=CH— | H | i-C$_3$H$_7$ | 3Br,4OH—C$_6$H$_3$ | — |
| 71 | —CH=N— | H | C$_2$H$_5$ | C$_6$H$_5$ | — |
| 72 | —CH=N— | H | CH$_2$—CH(CH$_3$)$_2$ | C$_6$H$_5$ | — |
| 73 | —N=CH— | H | i-C$_3$H$_7$ | 4-F—C$_6$H$_4$ | — |
| 74 | —CH=N— | H | C$_4$H$_9$ | 3-F—C$_6$H$_4$ | — |
| 75 | —CH=CH— | H | i-C$_3$H$_7$ | 3Cl,4OH—C$_6$H$_3$ | — |
| 76 | —N=CH— | H | i-C$_3$H$_7$ | C$_6$H$_5$ | — |
| 77 | —CH=N— | H | C$_3$H$_7$ | 2-CH$_3$—C$_6$H$_4$ | — |
| 78 | —N=CH— | H | i-C$_3$H$_7$ | 3-Cl—C$_6$H$_4$ | — |
| 79 | —CH=N— | H | CH$_2$—CH(CH$_3$)$_2$ | 2-CH$_3$—C$_6$H$_4$ | — |
| 80 | —CH=N— | H | C$_2$H$_5$ | 2-CH$_3$—C$_6$H$_4$ | — |
| 81 | —N=CH— | H | i-C$_3$H$_7$ | 3-F—C$_6$H$_4$ | — |
| 82 | —CH=N— | H | i-C$_3$H$_7$ | 2-F—C$_6$H$_4$ | — |
| 83 | —CH=N— | H | C$_4$H$_9$ | 2-CH$_3$—C$_6$H$_4$ | — |
| 84 | —CH=N— | H | C$_3$H$_7$ | 3-F—C$_6$H$_4$ | — |

EXAMPLE 9

To a stirred and cooled (0° C.) mixture of 8 parts of 4-(1H-imidazol-1-yl)methyl]-2-nitrobenzenamine and 106 parts of dichloromethane were added 3.4 ml of 4-methylene-2-oxetanone. After stirring for 1 hour at 0° C., another portion of 3.4 ml of 4-methylene-2-oxetanone was added and stirring was continued for 1 hour at this low temperature. The reaction mixture was diluted with 8 parts of methanol and evaporated to dry. The residue was crystallized from 2-propanone, yielding 7.6 parts (68.7%) of N-[4-(1H-imidazol-1-yl)methyl]-2-nitrophenyl]-3-oxobutanamide; mp. 172° C. (interm. 85).

In a similar manner there were also prepared:

TABLE 4

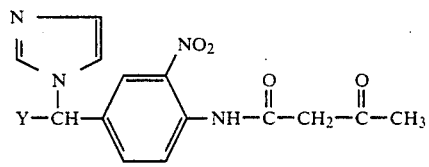

| Int. No. | Y | mp. |
|---|---|---|
| 86 | i-C$_3$H$_7$ | 85° C. |
| 87 | 3-Cl—C$_6$H$_4$ | — |
| 88 | c-C$_6$H$_{11}$ | — |
| 89 | 4-Cl—C$_6$H$_4$ | — |
| 90 | c-C$_5$H$_9$ | — |
| 91 | CH$_3$ | 134° C. |
| 92 | C$_2$H$_5$ | — |
| 93 | 4-F—C$_6$H$_4$ | — |
| 94 | 2-F—C$_6$H$_4$ | — |
| 95 | 3-F—C$_6$H$_4$ | — |

EXAMPLE 10

A solution of 10 parts of 4-[1-(1H-imidazol-1-yl)-2-methylpropyl]-2-nitrobenzenamine, 20 parts of ethyl β-oxobenzenepropanoate and 174 parts of benzene was stirred for 36 hours at reflux temperature. After cooling, the reaction mixture was evaporated. The residue was purified by column chromatography over silica gel using a mixture of dichloromethane and methanol (98:2 by volume) as eluent. The pure fractions were collected and the eluent was evaporated, yielding 7 parts (44.8%) of N-[4-[1-(1H-imidazol-1-yl)-2-methylpropyl]-2-nitrophenyl]-β-oxobenzenepropanamide; mp. 106° C. (interm. 96).

In a similar manner there were also prepared:
N-[4-[1-(1H-imidazol-1-yl)ethyl]-2-nitrophenyl]-β-oxobenzenepropanamide; mp. 172° C. (interm. 97);

N-[4-(1H-imidazol-1-ylmethyl)-2-nitrophenyl]-β-oxobenzenepropanamide; mp. 98° C. (interm. 98); and
N-[4-[(1H-imidazol-1-yl)phenylmethyl]-2-nitrophenyl]-β-oxobenzenepropanamide (interm. 99).

EXAMPLE 11

To a stirred solution of 13 parts of 4-[1-(1H-imidazol-1-yl)-2-methylpropyl]-2-nitrobenzenamine in 195 parts of dichloromethane was added a solution of 19 parts of 3-chlorobenzeneacetyl chloride in 65 parts of dichloromethane. After stirring for 4 hours at room temperature, 10.1 parts of N,N-diethylethanamine were added. The reaction mixture was washed with water, dried, filtered and evaporated, yielding 39 parts (100%) of 3-chloro-N-[4-[1-(1H-imidazol-1-yl)-2-methylpropyl]-2-nitrophenyl]benzeneacetamide as an oily residue (interm. 100).

In a similar manner there were also prepared:

TABLE 5

| Int. No. | —X¹=X²— | Y | X |
|---|---|---|---|
| 101 | —CH=CH— | i-C₃H₇ | 4-Cl |
| 102 | —CH=CH— | i-C₃H₇ | 4-F |
| 103 | —CH=N— | i-C₃H₇ | H |
| 104 | —CH=CH— | C₄H₉ | H |
| 105 | —CH=CH— | i-C₃H₇ | 3-F |
| 106 | —CH=CH— | 4-Cl—C₆H₄ | H |
| 107 | —CH=CH— | 3-Cl—C₆H₄ | H |
| 108 | —CH=CH— | i-C₃H₇ | 2-CH₃ |
| 109 | —CH=CH— | i-C₃H₇ | 3-OCH₃ |
| 110 | —CH=CH— | i-C₃H₇ | 3-CH₃ |
| 111 | —CH=CH— | i-C₃H₇ | 4-OC₂H₅ |

EXAMPLE 12

To a stirred and cooled (5° C.) solution of 10 parts of 4-[2-methyl-1-(1H-1,2,4-triazol-1-yl)propyl]-2-nitrobenzenamine and 6.7 parts of pyridine in 195 parts of dichloromethane was added a solution of 14.4 parts of 4-chlorobenzeneacetyl chloride in 39 parts of dichloromethane under nitrogen atmosphere. After stirring overnight at room temperature, the reaction mixture was washed with water, dried, filtered and evaporated. The residue was purified by column chromatography over silica gel using a mixture of dichloromethane and methanol (99:1 by volume) as eluent. The eluent of the desired fraction was evaporated, yielding 11 parts (69.9%) of 4-chloro-N-[4-[2-methyl-1-(1H-1,2,4-triazol-1-yl)propyl]-2-nitrophenyl]benzeneacetamide (interm. 112).

In a similar manner there were also prepared:
4-fluoro-N-[4-[2-methyl-1-(1H-1,2,4-triazol-1-yl)propyl]-2-nitrophenyl]benzeneacetamide (interm. 113);
3-fluoro-N-[4-[2-methyl-1-(1H-1,2,4-triazol-1-yl)propyl]-2-nitrophenyl]benzeneacetamide (interm. 114);
N-[4-[2-methyl-1-(1H-1,2,4-triazol-1-yl)propyl]-2-nitrophenyl]-3-thiopheneacetamide (interm. 115); and
3-chloro-N-[4-[2-methyl-1-(1H-1,2,4-triazol-1-yl)propyl]-2-nitrophenyl]benzeneacetamide (interm. 116).

EXAMPLE 13

A mixture of 31 parts of 4-[1-(1H-imidazol-1-yl)-2-methylpropyl]-2-nitrobenzenamine and 240 parts of ethanol was hydrogenated at 0.5.10⁵ Pa in a Parr apparatus and at room temperature with 30 parts of Raney nickel catalyst. After the calculated amount of hydrogen was taken up, the catalyst was filtered off over diatomaceous earth and the filtrate was evaporated, yielding 27.4 parts (100%) of 4-[1-(1H-imidazol-1-yl)-2-methylpropyl]-1,2-benzenediamine as a residue (interm. 117).

In a similar manner there were also prepared:

TABLE 6

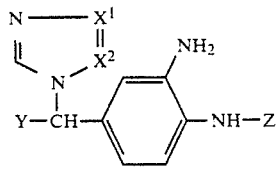

| Int. No. | —X¹=X²— | Z | Y |
|---|---|---|---|
| 118 | —CH=CH— | H | C₆H₅ |
| 119 | —CH=CH— | H | 3-pyridinyl |
| 120 | —CH=CH— | H | 2-thienyl |
| 121 | —CH=CH— | H | 4-F—C₆H₄ |
| 122 | —CH=CH— | H | 3-Cl—C₆H₄ |
| 123 | —CH=CH— | H | c-C₃H₅ |
| 124 | —CH=CH— | H | CH₃ |
| 125 | —CH=CH— | H | C₄H₉ |
| 126 | —CH=CH— | H | C₂H₅ |
| 127 | —CH=CH— | H | CH₂—CH(CH₃)₂ |
| 128 | —CH=CH— | CH₃ | i-C₃H₇ |
| 129 | —CH=CH— | H | C₃H₇ |
| 130 | —CH=CH— | H | 3-F—C₆H₄ |
| 131 | —CH=CH— | H | 2-Cl—C₆H₄ |
| 132 | —CH=CH— | H | 2-F—C₆H₄ |
| 132 | —CH=CH— | H | 4-CH₃—C₆H₄ |
| 133 | —CH=CH— | H | 3-CF₃—C₆H₄ |
| 134 | —CH=CH— | H | 4-Cl—C₆H₄ |
| 135 | —CH=N— | H | i-C₃H₇ |
| 136 | —CH=CH— | H | c-C₆H₁₁ |
| 137 | —CH=CH— | H | c-C₅H₉ |
| 138 | —CH=CH— | H | 4-(i-C₃H₇)—C₆H₄ |

B. PREPARATION OF THE FINAL COMPOUNDS

EXAMPLE 14

A mixture of 15.5 parts of 5-(bromomethyl)quinoxaline, 23.5 parts of 1H-imidazole and 160 parts of acetonitrile was stirred for 1.5 hours at reflux temperature. The reaction mixture was evaporated and the residue was taken up in water. The product was extracted three times with 65 parts of dichloromethane. The combined extracts were dried, filtered and evaporated. The residue was purified by column chromatography over silica gel using a mixture of dichloromethane and methanol (95:5 by volume) as eluent. The pure fractions were collected and the eluent was evaporated. The residue was crystallized from a mixture of 2-propanone and 2,2'-oxybispropane. The product was filtered off and dried, yielding 3 parts (20.5%) of 5-(1H-imidazol-1-ylmethyl)quinoxaline; mp. 121.2° C. (comp. 41).

EXAMPLE 15

A mixture of 10.4 parts of α-phenyl-6-quinoxalinemethanol methanesulfonate(ester), 12 parts of 1H-1,2,4-triazole and 79 parts of acetonitrile was stirred overnight at reflux temperature. The reaction mixture was evaporated and the residue was extracted with ethyl acetate. The extract was dried, filtered and evaporated. The residue was purified by column chromatography (silica gel; CH$_2$Cl$_2$/CH$_3$OH 96:4). The eluent of the desired fraction was evaporated and the residue was crystallized from a mixture of 2-propanol and 2,2'-oxybispropane, yielding 0.9 parts (9.5%) of 6-[phenyl(4H-1,2,4-triazol-4-yl)methyl]quinoxaline; mp. 98.1° C. (comp. 50).

EXAMPLE 16

A mixture of 7.8 parts of 6-quinoxalinecarboxaldehyde and 24.3 parts of 1,1'-carbonylbis-1H-imidazole was stirred for 1 hour at 100° C. After cooling, the reaction mixture was partitioned between water and ethyl acetate. The organic layer was dried, filtered and evaporated. The residue was purified by column chromatography (silica gel; CH$_2$Cl$_2$/CH$_3$OH/NH$_4$OH 85:15:1). The eluent of the desired fraction was evaporated and the residue was converted into the 4-methylbenzenesulfonate(1:2) salt in 2-propanone, yielding 7 parts (23.0%) of 6-[di(1H-imidazol-1-yl)methyl]quinoxaline 4-methylbenzenesulfonate(1:2); mp. 240.3° C. (comp. 51).

EXAMPLE 17

(a) A mixture of 3.76 parts of 4-(1H-imidazol-1-ylmethyl)-1,2-benzenediamine, 4.5 parts of diphenylethanedione and 80 parts of ethanol was stirred for 4 hours at reflux temperature. The reaction mixture was concentrated and the concentrate was purified by column chromatography over silica gel using a mixture of trichloromethane and methanol (95:5 by volume) as eluent. The pure fractions were collected and the eluent was evaporated. The residue was crystallized from a mixture of 1,1'-oxybisethane and ethanol. The product was filtered off and dried, yielding 4 parts (55%) of 6-(1H-imidazol-1-ylmethyl)-2,3-diphenylquinoxaline; mp. 159.3° C. (comp. 8).

(b) 6-[(1H-imidazol-1-yl)(phenyl)methyl]quinoxaline; mp. 126.8° C. (comp. 5) was prepared following substantially the same procedures as in example 17a except that ethanedial was used in place of diphenylethanedione, and 4-[(1H-imidazol-1-yl)phenylmethyl]-1,2-benzenediamine in place of 4-(1H-imidazol-1-ylmethyl)-1,2-benzenediamine.

(c) 6-[(1H-imidazol-1-yl)(phenyl)methyl]-2,3-dimethylquinoxaline monohydrate; mp. 82.9° C. (comp. 6) was prepared following substantially the same procedures as in example 17b except that 2,3-butanedione was used in place of ethanedial.

EXAMPLE 18

(a) A mixture of 8.1 parts of 4-[(3-fluorophenyl)(1H-imidazol-1-yl)methyl]-1,2-benzenediamine, 5 parts of ethanedial and 80 parts of methanol was stirred at reflux temperature. Upon complete reaction, the mixture was evaporated to dry and the residue was taken up in water. The product was extracted with trichloromethane. The extract was dried, filtered and evaporated. The residue was purified by column chromatography over silica gel using a mixture of dichloromethane and methanol (98:2 by volume) was eluent. The pure fractions were collected and the eluent was evaporated. The residue was crystallized from 2,2'-oxybispropane. The product was filtered off and dried, yielding 6.35 parts (74.5%) of 6-[(3-fluorophenyl)(1H-imidazol-1-yl)methyl]quinoxaline; mp. 109.7° C. (comp. 15).

(b) 6-[(3-fluorophenyl)-(1H-imidazol-1-yl)methyl]-2,3-dimethylquinoxaline; mp. 81.4° C. (comp. 19) was prepared following substantially the same procedures as in example 18a except that 2,3-butanedione was used in place of ethanedial.

EXAMPLE 19

To a cooled (0°-5° C.) solution of 4.5 parts of 6-[1-(1H-imidazol-1-yl)-2-methylpropyl]quinoxaline in 79 parts of methanol were added portionwise 4.5 parts of sodium tetrahydroborate. After stirring for 3 hours at 0°-5° C., water was added. The product was extracted with dichloromethane and the extract was dried, filtered and evaporated. The residue was purified by column chromatography (silica gel; CH$_2$Cl$_2$/CH$_3$OH/NH$_4$OH 90:10:0.1). The eluent of the desired fraction was evaporated and the residue was converted into the ethanedioate (2:5) salt in ethanol, yielding 1 part (11.5%) of 1,2,3,4-tetrahydro-6-[1-(1H-imidazol-1-yl)-2-methylpropyl]quinoxaline ethanedioate(2:5) hemihydrate; mp. 145.6° C. (comp. 1).

EXAMPLE 20

(a) A mixture of 9.1 parts of 4-[(3-chlorophenyl)(1H-imidazol-1-yl)methyl]-1,2-benzenediamine, 3.7 parts of ethyl 2-oxopropanoate and 160 parts of methanol was stirred for 30 minutes at reflux temperature. The reaction mixture was evaporated to dry. The residue was crystallized from a mixture of 36 parts of 2-propanone and 4 parts of methanol. After stirring for 30 minutes at room temperature, the precipitated product was filtered off (the filtrate was set aside) and recrystallized from a mixture of methanol and dichloromethane. The product was filtered off and dried, yielding 3 parts (28.1%) of 6-[(3-chlorophenyl)(1H-imidazol-1-yl)methyl]-3-methyl-2(1H)-quinoxalinone; mp. 270.9° C. (comp. 73). The filtrate (see above) was evaporated and the residue was purified by column chromatography over silica gel using a mixture of dichloromethane and methanol (95:5 by volume) as eluent. The pure fractions were collected and the eluent was evaporated. The residue was taken up in a mixture of 2-butanone and 2-propanone and the whole was allowed to stand for a few days. the precipitated product was filtered off and dried, yielding 1.4 parts (11.5%) of 7-[(3-chlorophenyl) (1H-imidazol-1-yl)methyl]-3-methyl-2(1H)-quinoxalinone hemihydrate; mp. 201.9° C. (comp. 81).

(b) 6-[1-(1H-imidazol-1-yl)-2-methylpropyl]-3-(2-methylpropyl)-2(1H)-quinoxalinone; mp. 197.4° C. (comp. 101) and 7-[1-(1H-imidazol-1-yl)-2-methylpropyl]-3-(2-methylpropyl)-2(1H)-quinoxalinone; mp. 173.5° C. (comp. 102) were prepared following substantially the same procedures as in example 20a except that ethyl 4-methyl-2-oxopentanoate was used in place of ethyl 2-oxopropanoate, and 4-[1-(1H-imidazol-1-yl)-2-methylpropyl]-1,2-benzenediamine in place of 4-[(3-chloro-phenyl)-(1H-imidazol-1-yl)methyl]-1,2-benzenediamine.

(c) 7-[1-(1H-imidazol-1-yl)-2-methylpropyl]-3-(1-methylethyl)-2(1H)-quinoxalinone; mp. 186.7° C. (comp. 106) and 6-[1-(1H-imidazol-1-yl)-2-methylpropyl]-3-(1-methylethyl)-2(1H)-quinoxalinone; mp. 187.4° C. (comp. 117) were prepared following substantially the same procedures as in example 20b except that ethyl 3-methyl-2-oxobutanoate was used in place of ethyl 4-methyl-2-oxopentanoate.

(d) 6-[1-(1H-imidazol-1-yl)-2-methylpropyl]-3-phenyl-2(1H)quinoxalinone; mp. 209.6° C. (comp. 89) and 7-[1-(1H-imidazol-1-yl)-2-methylpropyl]-3-phenyl-2(1H)quinoxalinone; mp. 281.0° C. (comp. 91) were prepared following substantially the same procedures as in example 20b except that methyl α-oxobenzenacetate was used in place of ethyl 4-methyl-2-oxopentanoate.

(e) ethyl 3,4-dihydro-7-(1H-imidazol-1ylmethyl)-α-methyl-3-oxo-2-quinoxalineacetate; mp. 208.1° C. (comp. 87) and ethyl 3,4-dihydro-6-(1H-imidazol-1yl-methyl)-α-methyl-3-oxo-2-quinoxalineacetate; mp. 223.4° C. (comp. 88) were prepared following substantially the same procedures as in example 20a except that diethyl 2-methyl-3-oxo-1,4-butanedioate was used in place of ethyl 2-oxopropanoate, and 4-[(1H-imidazol-1-yl)methyl]-1,2-benzenediamine in place of 4-[(3-chlorophenyl) (1H-imidazol-1-yl)methyl]-1,2-benzenediamine.

EXAMPLE 21

(a) To a stirred and cooled (0° C.) solution of 9.1 parts of 4-[(3-chlorophenyl)(1H-imidazol-1-yl)methyl]-1,2-benzenediamine in 80 parts of acetic acid and 20 parts of water were added portionwise 5.8 parts of ethyl 4-methyl-2-oxopentanoate. Upon completion, stirring was continued for 4 hours at room temperature. The reaction mixture was poured into 100 parts of water and the whole was neutralized with a sodium hydroxide solution 3N. The product was extracted with dichloromethane. The extract was dried, filtered and evaporated. The residue was purified by column chromatography over silica gel using a mixture of dichloromethane and methanol (95:5 by volume) as eluent. The pure fractions were collected and the eluent was evaporated. The residue was crystallized from a mixture of 2-propanone and 1,1'-oxybisethane. The product was filtered off (the filtrate was set aside) and dried, yielding 1.5 parts (12.6%) of 6-[(3-chlorophenyl) (1H-imidazol-1-yl)methyl]-3-(2-methylpropyl)-2(1H)-quinoxalinone; mp. 209.7° C. (comp. 178)

The filtrate (see above) was evaporated and the residue was further purified by column chromatography (HPLC) over silica gel using a mixture of dichloromethane and methanol (95:5 by volume) as eluent. The pure fractions were collected and the eluent was evaporated. The residue was crystallized twice, yielding 1.2 parts (10.0%) of 7-[(3-chlorophenyl)(1H-imidazol-1-yl)methyl]-3-(2-methylpropyl)-2(1H)-quinoxalinone; mp. 215.2° C. (comp. 177).

(b) 6-[(3-chlorophenyl)(1H-imidazol-1-yl)methyl]-3-(1-methylethyl)]-2(1H)-quinoxalinone; mp. 188.8° C. (comp. 181) and 7-[(3-chlorophenyl)(1H-imidazol-1-yl)methyl]-3-(1-methylethyl)]-2(1H)-quinoxalinone (comp. 313) were prepared following substantially the same procedures as in example 21a except that methyl 3-methyl-2-oxobutanoate was used in place of ethyl 4-methyl-2-oxopentanoate.

EXAMPLE 22

A mixture of 8.8 parts of 4-[1-(1H-imidazol-1-yl)-2-methylpropyl]-1,2-benzenediamine, 3 parts of 2-oxoacetic acid monohydrate and 80 parts of methanol was stirred for 4 hours at reflux temperature. The reaction mixture was evaporated to dry and the residue was purified by column chromatography over silica gel using a mixture of dichloromethane and methanol (98:2 by volume) as eluent. The fractions with the two isomers were collected and the eluent was evaporated. The isomers were separated by crystallization; first from a mixture of 2-butanone and 2-propanone and then from 2-butanone.

The first product was filtered off and dried, yielding 1.25 parts (12.3%) of 7-[1-(1H-imidazol-1-yl)-2-methylpropyl]-2(1H)-quinoxalinone; mp. 246.3° C. (comp. 90). The second product was filtered off and dried, yielding 0.5 parts (4.9%) of 6-[1-(1H-imidazol-1-yl)-2-methylpropyl]-2(1H)-quinoxalinone; mp. 193.9° C. (comp. 94).

EXAMPLE 23

(a) To a stirred and cooled (0° C.) mixture of 9 parts of 4-[1-(1H-imidazol-1-yl)-2-methylpropyl]-1,2-benzenediamine in 80 parts of acetic acid and 20 parts of water were added 5 parts of 2-oxopentanoic acid. The reaction mixture was stirred for 12 hours at room temperature. The whole was poured into ice water and neutralized with a sodium hydroxide solution 3N. The product was extracted three times with 130 parts of dichloromethane. The combined extracts were dried, filtered and evaporated. For obtaining 6-[1-(1H-imidazol-1yl)-2-methylpropyl]-3-propyl-2(1H)-quinoxalinone, the residue was purified by column chromatography (HPLC) over silica gel using a mixture of dichloromethane and methanol (98:2 by volume) as eluent. The pure fractions were collected and the eluent was evaporated. The residue was crystallized from a mixture of 2-butanone and 1,1'-oxybisethane. The precipitated product was filtered off and stirred in cold 4-methyl-2-pentanone. After filtration, the product was recrystallized from a mixture of methanol and 2-propanone, yielding 1.6 parts (13.2%) of the above product; mp. 259.7° C. (comp. 100).

For obtaining 7-[1-(1H-imidazol-1yl)-2-methylpropyl]-3-propyl-2(1H)-quinoxalinone, the residue was purified by column chromatography over silica gel using a mixture of dichloromethane, 2-propanol and ammonium hydroxide (90:10:0.1 by volume) as eluent. The pure fractions were collected and the eluent was evaporated. The residue was crystallized from a mixture of acetonitrile and 1,1'-oxybisethane. The precipitated product was filtered off and recrystallized first three times from a mixture of methanol and acetonitrile and then twice from a mixture of methanol, ethyl acetate and 2-propanol, yielding 1.45 parts (12.0%) of the above product; mp. 176.0° C. (comp. 140).

(b) 3-ethyl-6-[1-(1H-imidazol-1-yl)-2-methylpropyl]-2(1H)-quinoxalinone; mp. 203.7° C. (comp. 104) and 3-ethyl-7-[1-(1H-imidazol-1-yl)-2-methylpropyl]-2(1H)-quinoxalinone (comp. 314) were prepared following substantially the same procedures as in example 23a were used except that 2-oxobutanoic acid was used in place of 2-oxopentanoic acid.

EXAMPLE 24

A solution of 15 parts of 4-[1-(1H-imidazol-1-yl)-2-methylpropyl]-1,2-benzenediamine and 12.5 parts of diethyl 2-oxo-1,3-propanedioate in 80 parts of ethanol was stirred for 2 hours at reflux temperature. The reaction mixture was evaporated and the residue was purified by column chromatography over silica gel using a mixture of dichloromethane and methanol (95:5 by volume) as eluent. The pure fractions were collected and the eluent was evaporated. The residue was crystallized from a mixture of acetonitrile and ethanol. The product was filtered off and dried, yielding 3.1 parts (14.0%) of ethyl 3,4-dihydro-7-[1-(1H-imidazol-1-yl)-2-methylpropyl]-3-oxo-2-quinoxalinecarboxylate; mp. 229.7° C. (comp. 107).

The filtrate of the crystallization was evaporated and the residue was recrystallized from a mixture of acetonitrile and ethanol. The product was filtered off and dried, yielding 2.2 parts (10.0%) of ethyl 3,4-dihydro-6-[1-(1H-imidazol-1-yl)-2-methylpropyl]-3-oxo-2-quinoxalinecarboxylate; mp. 184.8° C. (comp. 116).

EXAMPLE 25

A mixture of 7 parts of N-[4-[1-(1H-imidazol-1-yl)-2-methylpropyl]-2-nitrophenyl]-β-oxobenzenepropanamide, 7.03 parts of potassium carbonate and 70 parts of water was stirred for 1.5 hours at reflux temperature. After cooling, the whole was treated with a hydrochloric acid solution 3N to pH 7. The product was extracted with dichloromethane (3×104 parts). The combined extracts were dried, filtered and evaporated. The residue was taken up in ethanol. The product was filtered off and dried, yielding 5.1 parts (73.0%) of 3-benzoyl-6-[1-(1H-imidazol-1-yl)-2-methylpropyl]-2(1H)-quinoxalinone, $N^4$-oxide monohydrate; mp. 210.0° C. (comp. 154).

EXAMPLE 26

A mixture of 12 parts of N-[4-[(3-chlorophenyl)(1H-imidazol-1-yl)methyl]-2-nitrophenyl]-3-oxobutanamide and 120 parts of sodium hydroxide solution 6.5% was stirred for 15 minutes at 80° C. After cooling, the product was obtained, yielding 10.25 parts (100%) of 6-[(3-chlorophenyl)(1H-imidazol-1-yl)methyl]-2(1H)-quinoxalinone, $N^4$-oxide (comp. 175).

EXAMPLE 27

To a stirred mixture of 11 parts of 4-chloro-N-[4-[2-methyl-1-(1H-1,2,4-triazol-1-yl)propyl]-2-nitrophenyl]-benzeneacetamide and 49 parts of pyridine were added 3.6 parts of 2-methyl-2-propanol, potassium salt under a nitrogen atmosphere. After stirring for 1 hour at room temperature, the reaction mixture was poured into ice-water. The whole was neutralized with HCl 3N and the product was extracted with dichloromethane. The extract was dried, filtered and evaporated. The residue was purified by column chromatography (silica gel; $CH_2Cl_2/CH_3OH$ 98:2). The eluent of the desired fraction was evaporated, yielding 6.6 parts (61.8%) of 3-(4-chlorophenyl)-6-[2-methyl-1-(1H-1,2,4-triazol-1-yl)propyl]-2(1H)-quinoxalinone, $N^4$-oxide (comp. 221).

EXAMPLE 28

A solution of 14.5 parts of 3-fluoro-N-[4-[1-(1H-imidazol-1-yl)-2-methylpropyl]-2-nitrophenyl]benzeneacetamide in 49 parts of pyridine and 10 parts of a potassium hydroxide solution 20% was stirred for 1 hour at 85° C. The reaction mixture was poured into crushed ice and neutralized with a sulfuric acid solution 2N. After evaporation, the residue was purified by column chromatography over silica gel using a mixture of dichloromethane, methanol and ammonium hydroxide (95:5:0.5 by volume) as eluent. The pure fractions were collected and the eluent was evaporated. The residue was crystallized from a mixture of dichloromethane and 2,2'-oxybispropane. The product was filtered off and dried, yielding 4.3 parts (67.6%) of 3-(3-fluorophenyl)-6-[1-(1H-imidazol-1-yl)-2-methylpropyl]-2(1H)-quinoxalinone, $N^4$-oxide; mp. 212.9° C. (comp. 166).

EXAMPLE 29

A mixture of 5 parts of 4-(1H-imidazol-1-ylmethyl)-1,2-benzenediamine, 4 parts of diethyl ethanedioate and 40 parts of methanol was stirred for 4 hours at room temperature. The precipitated product was filtered off and dried, yielding 4 parts (62.3%) of 6-(1H-imidazol-1-ylmethyl)-2,3(1H,4H)-quinoxalinedione; mp. >300° C. (comp. 315).

EXAMPLE 30

A solution of 3 parts of 6-[1-(1H-imidazol-1-yl)pentyl]-3-phenyl-2(1H)-quinoxalinone, $N^4$-oxide in 80 parts of methanol was hydrogenated over night at $2.10^5$ Pa and at room temperature with 0.5 parts of Raney nickel catalyst. The catalyst was filtered off over diatomaceous earth and the filtrate was evaporated. The residue was crystallized from acetonitrile, yielding 2.5 parts (87.2%) of 6-[1-(1H-imidazol-1-yl)pentyl]-3-phenyl-2(1H)-quinoxalinone; mp. 192.4° C. (comp. 162).

EXAMPLE 31

A mixture of 10.25 parts of 6-[(3-chlorophenyl)(1H-imidazol-1-yl)methyl]-2(1H)-quinoxalinone, $N^4$-oxide, 120 parts of a sodium hydroxide solution 6.5% and 120 parts of water was hydrogenated for 1 hour in a Parr apparatus at $3.10^5$ Pa and at room temperature with 10 parts of a Raney nickel catalyst under nitrogen atmosphere. The whole was filtered over diatomaceous earth and the filtrate was treated with a hydrochloric acid solution 3N to pH 7. The product was extracted with a mixture of dichloromethane and methanol. The extract was dried, filtered and evaporated. The residue was purified by column chromatography over silica gel using a mixture of dichloromethane and methanol (96:4 by volume) as eluent. The pure fractions were collected and the eluent was evaporated. The residue was crystallized from a mixture of 2-butanone, 2-propanone and 1,1'-oxybisethane. The product was filtered off and dried, yielding 0.95 parts (9.7%) of 6-[(3-chlorophenyl)(1H-imidazol-1-yl)methyl]-2(1H)-quinoxalinone; mp. 253.0° C. (comp. 176).

EXAMPLE 32

A mixture of 3.9 parts of 3-(3,4-dimethoxyphenyl)-6-[1-(1H-imidazol-1-yl)-2-methylpropyl]-2(1H)-quinoxalinone, $N^4$-oxide, 3.3 parts of sodium dithionate, 55.3 parts of ethanol and 30 parts of water was refluxed for ½ hour. After cooling, the reaction mixture was partitioned between water and dichloromethane. The organic layer was dried, filtered and evaporated. The residue was purified by column chromatography (silica gel; $CH_2Cl_2/CH_3OH$ 95:5). The eluent of the desired fraction was evaporated and the residue was crystallized from methanol and ethyl acetate, yielding 2.1 parts (56.4%) of 3-(3,4-dimethoxyphenyl)-6-[1-(1H-imidazol-1-yl)-2-methylpropyl]-2(1H)-quinoxalinone; mp. 242.6° C. (comp. 236).

EXAMPLE 33

A mixture of 3 parts of 7-(1H-imidazol-1-ylmethyl)-3-methyl-2(1H)-quinoxalinone, 0.3 parts of a sodium hydroxide dispersion 50% and 28 parts of N,N-dimethylformamide was stirred for 1.5 hours at room temperature. 2 Parts of iodomethane were added and stirring was continued for 12 hours at room temperature under nitrogen atmosphere. The reaction mixture was evaporated to dry and the residue was taken up in water and potassium carbonate. The product was extracted with dichloromethane. The extract was dried, filtered and evaporated. The residue was purified by column chromatography over silica gel using a mixture of dichloromethane and methanol (98:2 by volume) as eluent. The pure fractions were collected and the eluent was evaporated. The residue was crystallized from a mixture of 2,2'-oxybispropane and 2-propanone. The product was filtered off and dried, yielding 2.2 parts (66.8%) of 7-(1H-imidazol-1-ylmethyl)-1,3-dimethyl-2(1H)-quinoxalinone hemihydrate; mp. 128.6° C. (comp. 79).

EXAMPLE 34

A mixture of 5 parts of 6-[(1H-imidazol-1-yl)phenylmethyl]-3-methyl-2(1H)-quinoxalinone, 3.3 parts of sodium hydroxide and 30 parts of water was stirred for 1 hour at room temperature. 5 Parts of hydroxylamine-O-sulfonic acid were added and the reaction mixture was stirred for 4 hours at 20° C. The product was extracted with dichloromethane (3×65 parts). The combined extracts were dried, filtered and evaporated. The residue was purified by column chromatography over silica gel using a mixture of dichloromethane and methanol (95:5 by volume) as eluent. The pure fractions were collected and the eluent was evaporated. The residue was crystallized from a mixture of 2-propanone and 1,1'-oxybisethane. The product was filtered off and dried, yielding 2 parts (38.2%) of 1-amino-6-[(1H-imidazol-1-yl)phenylmethyl]-3-methyl-2(1H)-quinoxalinone; mp. 192.8° C. (comp. 85).

EXAMPLE 35

A solution of 4.25 parts of ethyl 3,4-dihydro-7-[1-(1H-imidazol-1-yl)-2-methylpropyl]-3-oxo-2-quinoxalinecarboxylate in 20 parts of a sodium hydroxide solution 1N was stirred for 4 hours at room temperature. The reaction mixture was treated with a diluted sulfuric acid solution to pH 5.5. After concentration, the residue was crystallized from pyridine. The product was filtered off and dried, yielding 1 part (24.6%) of 3,4-dihydro-7-[1-(1H-imidazol-1-yl)-2-methylpropyl]-3-oxo-2-quinoxalinecarboxylic acid; mp. 237.5° C. (comp. 129).

EXAMPLE 36

A mixture of 6 parts of 7-(1H-imidazol-1-ylmethyl)-3-methyl-2(1H)-quinoxalinone and 40 parts of phosphoryl chloride was stirred for 2 hours at reflux temperature. The reaction mixture was evaporated to dry. The residue was taken up in 300 parts of ice water and the whole was neutralized with potassium carbonate. The product was extracted three times with 65 parts of dichloromethane. The combined extracts were dried, filtered and evaporated. The residue was purified by column chromatography over silica gel using a mixture of dichloromethane and methanol (98:2 by volume) as eluent. The pure fractions were collected and the eluent was evaporated. The residue was crystallized from 1,1'-oxybisethane. The product was filtered off and dried, yielding 1.6 parts (59.4%) of 3-chloro-6-(1H-imidazol-1-ylmethyl)-2-methylquinoxaline; mp. 115.8° C. (comp. 22).

EXAMPLE 37

A solution of 0.3 parts of sodium in 24 parts of 1-propanol was added to 2.4 parts of 3-chloro-6-(1H-imidazol-1-ylmethyl)-2-methylquinoxaline. The whole was stirred for 2 hours at reflux temperature. The reaction mixture was evaporated and the residue was extracted three times with 65 parts of dichloromethane. The combined extracts were dried, filtered and evaporated. The residue was purified by column chromatography over silica gel using a mixture of dichloromethane and methanol (98:2 by volume) as eluent. The pure fractions were collected and the eluent was evaporated. The residue was crystallized from a mixture of pentane and 2,2'-oxybispropane. The product was filtered off and dried, yielding 1.5 parts (57.1%) of 6-(1H-imidazol-1-ylmethyl)-2-methyl-3-propoxyquinoxaline; mp. 85.5° C. (comp. 24).

EXAMPLE 38

A mixture of 5.5 parts of 3-chloro-6-[1-(1H-imidazol-1-yl)-2-methylpropyl]-2-methylquinoxaline, 9 parts of an aqueous N-methylmethanamine solution 40% and 48 parts of methanol was stirred for 12 hours at 140° C. After cooling, the reaction mixture was evaporated to dry and the residue was purified by column chromatography over silica gel using a mixture of dichloromethane and methanol (98:2 by volume) as eluent. The pure fractions were collected and the eluent was evaporated. The residue was crystallized from petroleum ether. The product was filtered off and dried, yielding 0.9 parts (15.9%) of 7-[1-(1H-imidazol-1-yl)-2-methylpropyl]-N,N,3-trimethyl-2-quinoxazolinamine; mp. 116.7° C. (comp. 47).

All other compounds listed in tables 7–11 were obtained by analogous methods of preparation as described in examples 14–38, the actual method of preparation being indicated in column 2 (Ex. No.)

TABLE 7

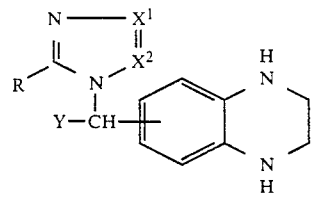

| Comp. No. | Ex. No. | R | —X$^1$=X$^2$ | Y | mp.(°C.)/base/salt |
|---|---|---|---|---|---|
| 1 | 19 | H— | —CH=CH— | i-C$_3$H$_7$— | 145.6° C./0.5H$_2$O/ 2.5(COOH)$_2$ |
| 2 | — | H— | —CH=CH— | H— | — |
| 3 | — | H— | —CH=CH— | C$_6$H$_5$— | — |
| 4 | — | H— | —CH=CH— | 4Cl—C$_6$H$_4$— | — |

TABLE 8

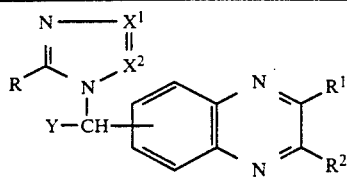

| Comp. No. | Ex. No. | R | $-X^1=X^2-$ | Y | p | $R^1$ | $R^2$ | mp. (°C.)/ base/salt |
|---|---|---|---|---|---|---|---|---|
| 5 | 17 | H— | —CH=CH— | $C_6H_5$— | 6 | H— | H— | 126.8 |
| 6 | 17 | H— | —CH=CH— | $C_6H_5$— | 6 | $CH_3$— | $CH_3$— | 82.9/$H_2O$ |
| 7 | 17 | H— | —CH=CH— | $CH_3$— | 6 | H— | H— | 135.1 |
| 8 | 17 | H— | —CH=CH— | H— | 6 | $C_6H_5$— | $C_6H_5$— | 159.3 |
| 9 | 18 | H— | —CH=CH— | $i$-$C_3H_7$— | 6 | H— | H— | 128.6 |
| 10 | 18 | H— | —CH=CH— | H— | 6 | H— | H— | 144.1 |
| 11 | 18 | H— | —CH=CH— | 4F—$C_6H_4$— | 6 | H— | H— | 131.6 |
| 12 | 18 | H— | —CH=CH— | $C_2H_5$— | 6 | H— | H— | 72.4 |
| 13 | 18 | H— | —CH=CH— | 2-thienyl | 6 | H— | H— | 93.7 |
| 14 | 18 | H— | —CH=CH— | 4F—$C_6H_4$— | 6 | $CH_3$— | $CH_3$— | 82.0/$H_2O$ |
| 15 | 18 | H— | —CH=CH— | 3F—$C_6H_4$— | 6 | H— | H— | 109.7 |
| 16 | 18 | H— | —CH=CH— | 2F—$C_6H_4$— | 6 | H— | H— | 79.7 |
| 17 | 18 | H— | —CH=CH— | $CH_3$— | 6 | $CH_3$— | $CH_3$— | 76.2/0.5$H_2O$ |
| 18 | 18 | H— | —CH=CH— | 3Cl—$C_6H_4$— | 6 | H— | H— | 70.3/0.5$H_2O$ |
| 19 | 18 | H— | —CH=CH— | 3F—$C_6H_4$— | 6 | $CH_3$— | $CH_3$— | 81.4 |
| 20 | 36 | H— | —CH=CH— | $C_6H_5$— | 6 | Cl— | $CH_3$— | 164.7 |
| 21 | 37 | H— | —CH=CH— | $C_6H_5$— | 6 | $CH_3O$— | $CH_3$— | 117.7 |
| 22 | 36 | H— | —CH=CH— | H— | 7 | Cl— | $CH_3$— | 115.8 |
| 23 | 37 | H— | —CH=CH— | H— | 7 | $CH_3O$— | $CH_3$— | 151.8 |
| 24 | 37 | H— | —CH=CH— | H— | 7 | $C_3H_7O$— | $CH_3$— | 85.5 |
| 25 | 37 | H— | —CH=CH— | H— | 7 | $i$-$C_3H_7O$— | $CH_3$— | 109.6 |
| 26 | 36 | H— | —CH=CH— | H— | 6 | Cl— | $CH_3$— | — |
| 27 | 37 | H— | —CH=CH— | H— | 6 | $C_3H_7O$— | $CH_3$— | 132.0 |
| 28 | 37 | H— | —CH=CH— | H— | 6 | $i$-$C_3H_7O$— | $CH_3$— | 117.5 |
| 29 | 37 | H— | —CH=CH— | H— | 7 | 1H-imidazolyl | $CH_3$— | 164.1 |
| 30 | 18 | H— | —CH=CH— | 2F—$C_6H_4$— | 6 | $CH_3$— | $CH_3$— | 94.5 |
| 31 | 37 | H— | —CH=CH— | H— | 6 | $CH_3O$— | $CH_3$— | 150.7 |
| 32 | 37 | H— | —CH=CH— | $C_6H_5$— | 6 | $C_3H_7O$— | $CH_3$— | 125.6 |
| 33 | 36 | H— | —CH=CH— | H— | 7 | Cl— | H— | — |
| 34 | 37 | H— | —CH=CH— | H— | 7 | $CH_3O$— | H— | 121.0 |
| 35 | 18 | H— | —CH=CH— | 2Cl—$C_6H_4$— | 6 | H— | H— | 114.7 |
| 36 | 36 | H— | —CH=CH— | $C_6H_5$— | 7 | Cl— | $CH_3$— | — |
| 37 | 37 | H— | —CH=CH— | $C_6H_5$— | 7 | $CH_3O$— | $CH_3$— | 131.2 |
| 38 | 36 | H— | —CH=CH— | H— | 6 | Cl— | H— | — |
| 39 | 37 | H— | —CH=CH— | H— | 6 | $CH_3O$— | H— | 123.2 |
| 40 | 18 | H— | —CH=CH— | 4$CH_3$—$C_6H_4$— | 6 | H— | H— | 132.9 |
| 41 | 14 | H— | —CH=CH— | H— | 5 | H— | H— | 121.2 |
| 42 | 18 | H— | —CH=CH— | 3$CF_3$—$C_6H_4$— | 6 | H— | H— | 96.5/$H_2O$ |
| 43 | 36 | H— | —CH=CH— | $i$-$C_3H_7$— | 6 | Cl— | $CH_3$— | — |
| 44 | 38 | H— | —CH=CH— | $i$-$C_3H_7$— | 6 | $NH_2$— | $CH_3$— | 238.2 |
| 45 | 36 | H— | —CH=CH— | $i$-$C_3H_7$— | 7 | Cl— | $CH_3$— | — |
| 46 | 37 | H— | —CH=CH— | $i$-$C_3H_7$— | 7 | $CH_3O$— | $CH_3$— | 124.6 |
| 47 | 38 | H— | —CH=CH— | $i$-$C_3H_7$— | 7 | $(CH_3)_2N$— | $CH_3$— | 116.7 |
| 48 | 15 | $CH_3$— | —CH=CH— | $C_6H_5$— | 6 | H— | H— | 134.5 |
| 49 | 15 | H— | —CH=N— | $C_6H_5$— | 6 | H— | H— | 96.0 |
| 50 | 15 | H— | —N=CH— | $C_6H_5$— | 6 | H— | H— | 98.1 |
| 51 | 16 | H— | —CH=CH— | 1H-imidazol-1-yl | 6 | H— | H— | 240.3/2* |
| 52 | — | H— | —CH=N— | $C_6H_5$— | 6 | $CH_3$— | $CH_3$— | — |
| 53 | — | H— | —CH=N— | $i$-$C_3H_7$— | 6 | $CH_3$— | $CH_3$— | — |
| 54 | — | $CH_3$— | —CH=CH— | $i$-$C_3H_7$— | 6 | H— | H— | — |
| 55 | — | H— | —CH=CH— | $CH_3$—C≡C— | 6 | H— | H— | — |
| 56 | — | H— | —CH=CH— | $CH_3$—CH=CH— | 6 | H— | H— | — |

* = 4-methylbenzenesulfonate

In the previous and following tables p indicates the position of the 1H-azol-1-yl-methyl moiety on the quinoxaline ring.

TABLE 9

| Comp. No. | Ex. No. | R | $-X^1=X^2-$ | Y | p | $R^3$ | $R^4$ | n | mp.(°C.)/base/salt |
|---|---|---|---|---|---|---|---|---|---|
| 57 | 20 | H— | —CH=CH— | $C_6H_5$— | 6 | H— | $CH_3$— | 0 | 254.0 |
| 58 | 20 | H— | —CH=CH— | H— | 7 | H— | $CH_3$— | 0 | 297.6 |
| 59 | 20 | H— | —CH=CH— | H— | 6 | H— | $CH_3$— | 0 | 271.3 |
| 60 | 20 | H— | —CH=CH— | $C_6H_5$— | 7 | H— | $CH_3$— | 0 | 218.4 |
| 61 | 22 | H— | —CH=CH— | H— | 7 | H— | H— | 0 | 253.6 |
| 62 | 22 | H— | —CH=CH— | H— | 6 | H— | H— | 0 | 272.9 |
| 63 | 34 | H— | —CH=CH— | 3-$CF_3$—$C_6H_4$— | 6 | $NH_2$— | $CH_3$— | 0 | 178.8 |
| 64 | 20 | H— | —CH=CH— | $CH_3$— | 7 | H— | $CH_3$— | 0 | >300(dec.) |
| 65 | 20 | H— | —CH=CH— | H— | 6 | H— | $C_6H_5$— | 0 | 268.2 |
| 66 | 20 | H— | —CH=CH— | H— | 7 | H— | $C_6H_5$— | 0 | 293.8 |
| 67 | 20 | H— | —CH=CH— | 2F—$C_6H_4$— | 6 | H— | $CH_3$— | 0 | 203.1 |
| 68 | 20 | H— | —CH=CH— | 3F—$C_6H_4$— | 6 | H— | $CH_3$— | 0 | 273.5 |
| 69 | 20 | H— | —CH=CH— | 4F—$C_6H_4$— | 6 | H— | $CH_3$— | 0 | 275.0 |
| 70 | 20 | H— | —CH=CH— | i-$C_3H_7$— | 6 | H— | $CH_3$— | 0 | 271.7 |
| 71 | 33 | H— | —CH=CH— | H— | 6 | $CH_3$— | $CH_3$— | 0 | 249.8 |
| 72 | 20 | H— | —CH=CH— | 3Cl—$C_6H_4$— | 6 | H— | $CH_3$— | 0 | 191.0 |
| 73 | 33 | H— | —CH=CH— | H— | 7 | $CH_3$— | $CH_3$— | 0 | 270.9 |
| 74 | 33 | H— | —CH=CH— | H— | 7 | $C_4H_9$— | $CH_3$— | 0 | 116.0 |
| 75 | 20 | H— | —CH=CH— | $C_6H_5$— | 6 | $C_4H_9$— | $CH_3$— | 0 | 139.9 |
| 76 | 20 | H— | —CH=CH— | $C_6H_5$— | 6 | $CH_3$— | $CH_3$— | 0 | 214.5 |
| 77 | 20 | H— | —CH=CH— | i-$C_3H_7$— | 6 | $CH_3$— | $CH_3$— | 0 | 192.5 |
| 78 | 20 | H— | —CH=CH— | $C_3H_7$— | 6 | H— | $CH_3$— | 0 | 234.0 |
| 79 | 33 | H— | —CH=CH— | H— | 6 | $CH_3$— | $CH_3$— | 0 | 128.6/0.5$H_2O$ |
| 80 | 33 | H— | —CH=CH— | H— | 6 | $C_4H_9$— | $CH_3$— | 0 | 128.4 |
| 81 | 20 | H— | —CH=CH— | 3Cl—$C_6H_4$— | 7 | H— | $CH_3$— | 0 | 201.9/0.5$H_2O$ |
| 82 | 20 | H— | —CH=CH— | $CH_3$— | 6 | H— | $CH_3$— | 0 | 228.8 |
| 83 | 20 | H— | —CH=CH— | 3F—$C_6H_4$— | 7 | H— | $CH_3$— | 0 | 209.9 |
| 84 | 20 | H— | —CH=CH— | 4F—$C_6H_4$— | 7 | H— | $CH_3$— | 0 | 177.3/0.5$H_2O$ (COOH)$_2$ |
| 85 | 34 | H— | —CH=CH— | $C_6H_5$— | 6 | $NH_2$— | $CH_3$— | 0 | 192.8 |
| 86 | 22 | H— | —CH=CH— | $C_6H_5$— | 6 | H— | H— | 0 | 225.0 |
| 87 | 20 | H— | —CH=CH— | H— | 6 | H— | * | 0 | 208.1 |
| 88 | 20 | H— | —CH=CH— | i-$C_3H_7$— | 7 | H— | $C_6H_5$— | 0 | 223.4 |
| 89 | 20 | H— | —CH=CH— | i-$C_3H_7$— | 6 | H— | H— | 0 | 209.6 |
| 90 | 22 | H— | —CH=CH— | i-$C_3H_7$— | 7 | H— | $C_6H_5$— | 0 | 246.3 |
| 91 | 20 | H— | —CH=CH— | H— | 6 | $NH_2$— | $CH_3$— | 0 | 281.0 |
| 92 | 34 | H— | —CH=CH— | H— | 6 | $NH_2$— | $CH_3$— | 0 | 220.7 |
| 93 | 20 | H— | —CH=CH— | 3-pyridinyl | 6 | H— | $CH_3$— | 0 | 237.4/0.5$H_2O$ |
| 94 | 22 | H— | —CH=CH— | i-$C_3H_7$— | 6 | H— | H— | 0 | 198.2 |

TABLE 9-continued

| Comp. No. | Ex. No. | R | —X¹=X²— | Y | p | R³ | R⁴ | n | mp.(°C.)/base/salt |
|---|---|---|---|---|---|---|---|---|---|
| 95 | 22 | H— | —CH=CH— | C₆H₅— | 7 | H— | H— | 0 | 187.6 |
| 96 | 20 | H— | —CH=CH— | C₆H₅— | 6 | H— | C₆H₅— | 0 | 251.0 |
| 97 | 20 | H— | —CH=CH— | c-C₃H₅— | 6 | H— | CH₃— | 0 | 275.4 |
| 98 | 20 | H— | —CH=CH— | i-C₄H₉— | 7 | H— | CH₃— | 0 | 205.4 |
| 99 | 20 | H— | —CH=CH— | C.C₃H₅— | 7 | H— | CH₃ | 0 | 203.0 |
| 100 | 23 | H— | —CH=CH— | i-C₃H₇— | 6 | H— | C₃H₇— | 0 | 259.7 |
| 101 | 20 | H— | —CH=CH— | i-C₃H₇— | 7 | H— | i-C₄H₉— | 0 | 197.4 |
| 102 | 20 | H— | —CH=CH— | i-C₃H₇— | 6 | H— | i-C₄H₉— | 0 | 173.5 |
| 103 | 20 | H— | —CH=CH— | C₂H₅— | 6 | H— | CH₃— | 0 | 211.9 |
| 104 | 23 | H— | —CH=CH— | i-C₃H₇— | 7 | H— | C₂H₅— | 0 | 203.7 |
| 105 | 20 | H— | —CH=CH— | C₄H₉— | 7 | H— | CH₃— | 0 | 189.0 |
| 106 | 20 | H— | —CH=CH— | i-C₃H₇— | 7 | H— | i-C₃H₇ | 0 | 186.7 |
| 107 | 20 | H— | —CH=CH— | i-C₃H₇— | 6 | H— | —COOC₂H₅ | 0 | 229.7 |
| 108 | 20 | H— | —CH=CH— | i-C₃H₇— | 6 | CH₃— | CH₃— | 0 | 132.6/0.5H₂O |
| 109 | 20 | H— | —CH=CH— | C₂H₅— | 6 | H— | CH₃— | 0 | 197.4 |
| 110 | 20 | H— | —CH=CH— | C₄H₉— | 6 | H— | CH₃— | 0 | 201.6 |
| 111 | 20 | H— | —CH=CH— | 4-Cl—C₆H₄— | 6 | H— | CH₃— | 0 | 228.7 |
| 112 | 20 | H— | —CH=CH— | 4-Cl—C₆H₄— | 7 | H— | CH₃— | 0 | 160.8 |
| 113 | 20 | H— | —CH=CH— | 4-CH₃O—C₆H₄— | 6 | H— | CH₃— | 0 | 199.7 |
| 114 | 23 | H— | —CH=CH— | C₆H₅— | 6 | H— | C₂H₅— | 0 | 280.0 |
| 115 | 23 | H— | —CH=CH— | C₆H₅— | 7 | H— | C₂H₅— | 0 | 211.2 |
| 116 | 24 | H— | —CH=CH— | i-C₃H₇— | 6 | H— | —COOC₂H₅ | 0 | 184.8 |
| 117 | 20 | H— | —CH=CH— | i-C₃H₇— | 7 | H— | i-C₃H₇— | 0 | 187.4 |
| 118 | 22 | H— | —CH=CH— | 4-CH₃—C₆H₄— | 7 | H— | H— | 0 | 203.6 |
| 119 | 20 | H— | —CH=CH— | 4-CH₃—C₆H₄— | 6 | H— | CH₃— | 0 | 150.4 |
| 120 | 20 | H— | —CH=CH— | 4-CH₃—C₆H₄— | 7 | H— | CH₃— | 0 | 222.5 |
| 121 | 20 | H— | —CH=CH— | C₃H₇— | 6 | H— | CH₃— | 0 | 143.1 |
| 122 | 22 | H— | —CH=CH— | 2-thienyl | 7 | H— | H— | 0 | 223.1 |
| 123 | 20 | H— | —CH=CH— | 2-thienyl | 6 | H— | CH₃— | 0 | 254.5 |
| 124 | 20 | H— | —CH=CH— | 4-CH₃O—C₆H₄— | 7 | H— | CH₃— | 0 | 203.5 |
| 125 | 20 | H— | —CH=N— | i-C₃H₇— | 7 | H— | CH₃— | 0 | 204.8 |
| 126 | 20 | H— | —CH=CH— | c-C₆H₁₁— | 6 | H— | CH₃— | 0 | 174.8 |
| 127 | 20 | H— | —CH=CH— | c-C₃H₅— | 7 | H— | C₆H₅— | 0 | >300 |
| 128 | 20 | H— | —CH=CH— | 2-thienyl | 6 | H— | C₆H₅— | 0 | 229.6 |
| 129 | 20 | H— | —CH=CH— | i-C₃H₇— | 7 | H— | CH₃— | 0 | 237.5 |
| 130 | 35 | H— | —CH=CH— | c-C₃H₅— | 6 | H— | HOOC— | 0 | 234.6 |
| 131 | 22 | H— | —CH=CH— | c-C₃H₅— | 7 | H— | H— | 0 | 168.5 |
| 132 | 20 | H— | —CH=CH— | CH₃— | 6 | H— | C₆H₅— | 0 | >300 |
| 133 | 22 | H— | —CH=CH— | c-C₃H₅— | 6 | H— | H— | 0 | 224.2 |

TABLE 9-continued

| Comp. No. | Ex. No. | R | —X¹=X²— | Y | p | R³ | R⁴ | n | mp.(°C.)/ base/salt |
|---|---|---|---|---|---|---|---|---|---|
| 134 | 20 | H— | —CH=CH— | c-C₅H₉— | 6 | H— | C₆H₅— | 0 | 127.9 |
| 135 | 20 | H— | —CH=CH— | c-C₆H₁₁— | 6 | H— | C₆H₅— | 0 | 193.4 |
| 136 | 22 | H— | —CH=CH— | CH₃— | 7 | H— | H— | 0 | 252.4 |
| 137 | 20 | H— | —CH=CH— | C₂H₅— | 6 | H— | C₆H₅— | 0 | >300 |
| 138 | 22 | H— | —CH=CH— | C₃H₇— | 6 | H— | H— | 0 | 161.9 |
| 139 | 22 | H— | —CH=CH— | c-C₆H₁₁— | 7 | H— | H— | 0 | 278.9 |
| 140 | 23 | H— | —CH=CH— | i-C₃H₇— | 6 | H— | C₃H₇— | 0 | 176.0 |
| 141 | 20 | H— | —CH=CH— | i-C₃H₇— | 6 | H— | C₆H₅— | 0 | 245.0 |
| 142 | 22 | H— | —CH=CH— | C₂H₅— | 7 | H— | H— | 0 | 201.3 |
| 143 | 22 | H— | —CH=CH— | c-C₅H₉— | 7 | H— | H— | 0 | >300 |
| 144 | 22 | H— | —CH=CH— | C₄H₉— | 7 | H— | H— | 0 | 170.0 |
| 145 | 20 | H— | —CH=CH— | C₄H₉— | 6 | H— | H— | 0 | 198.4 |
| 146 | 20 | H— | —CH=CH— | c-C₅H₉— | 6 | H— | C₆H₅— | 0 | 221.1 |
| 147 | 20 | H— | —CH=CH— | C₃H₇— | 6 | H— | CH₃— | 0 | 249.4 |
| 148 | 22 | H— | —CH=N— | i-C₃H₇— | 6 | H— | C₆H₅— | 0 | 209.2 |
| 149 | 20 | H— | —CH=CH— | i-C₃H₇— | 7 | H— | H— | 0 | 211.0 |
| 150 | 20 | H— | —CH=CH— | C₂H₅— | 6 | H— | C₆H₅— | 0 | 272.2 |
| 151 | 26 | H— | —CH=CH— | i-C₃H₇— | 6 | H— | H— | 1 | 208.7 |
| 152 | 25 | H— | —CH=CH— | CH₃— | 6 | H— | C₆H₅—CO— | 1 | 260.4 |
| 153 | 25 | H— | —CH=CH— | H— | 6 | H— | C₆H₅—CO— | 1 | 250.4 |
| 154 | 25 | H— | aCH=CH— | i-C₃H₇— | 6 | H— | C₆H₅—CO— | 1 | 210.0/H₂O |
| 155 | 28 | H— | —CH=CH— | i-C₃H₇— | 6 | H— | 4Cl—C₆H₄— | 1 | 181.3 |
| 156 | 28 | H— | —CH=CH— | i-C₃H₇— | 6 | H— | 4F—C₆H₄— | 1 | 205.3 |
| 157 | 30 | H— | —CH=CH— | i-C₃H₇— | 7 | H— | 4F—C₆H₄— | 0 | 240.8 |
| 158 | 28 | H— | —CH=N— | i-C₃H₇— | 6 | H— | C₆H₅— | 1 | — |
| 159 | 30 | H— | —CH=N— | i-C₃H₇— | 6 | H— | C₆H₅— | 0 | 249.4 |
| 160 | 30 | H— | —CH=CH— | i-C₃H₇— | 6 | H— | 4Cl—C₆H₄— | 0 | 236.6 |
| 161 | 28 | H— | —CH=CH— | C₄H₉— | 6 | H— | C₆H₅— | 1 | 240.5 |
| 162 | 30 | H— | —CH=CH— | C₄H₉— | 6 | H— | C₆H₅— | 0 | 192.4 |
| 163 | 30 | H— | —CH=CH— | i-C₃H₇— | 6 | H— | C₆H₅—CO— | 0 | 161.5/0.5H₂O |
| 164 | 28 | H— | —CH=CH— | i-C₃H₇— | 6 | H— | 3Cl—C₆H₄— | 1 | 177.4 |
| 165 | 30 | H— | —CH=CH— | i-C₃H₇— | 6 | H— | 3Cl—C₆H₄— | 0 | 179.7/H₂O |
| 166 | 28 | H— | —CH=CH— | i-C₃H₇— | 6 | H— | 3F—C₆H₄— | 1 | 212.9 |
| 167 | 30 | H— | —CH=CH— | i-C₃H₇— | 6 | H— | 3F—C₆H₄— | 0 | 255.6 |
| 168 | 28 | H— | —CH=CH— | H— | 6 | H— | C₆H₅—CO— | 1 | 268.9 |
| 169 | 30 | H— | —CH=CH— | CH₃— | 6 | H— | C₆H₅—CO— | 0 | 192.8 |
| 170 | 28 | H— | —CH=CH— | CH₃— | 6 | H— | H— | 1 | 186.2 |
| 171 | 26 | H— | —CH=CH— | 4Cl—C₆H₄— | 6 | H— | H— | 1 | — |
| 172 | 30 | H— | —CH=CH— | 4Cl—C₆H₄— | 6 | H— | C₆H₅— | 0 | 166.3/0.5H₂O |

TABLE 9-continued

| Comp. No. | Ex. No. | R | —X¹=X²— | Y | p | R³ | R⁴ | n | mp.(°C.)/ base/salt |
|---|---|---|---|---|---|---|---|---|---|
| 173 | 20 | H— | —CH=CH— | 4-iC₃H₇—C₆H₄— | 6 | H— | CH₃— | 0 | 237.6 |
| 174 | 20 | H— | —CH=CH— | 4-iC₃H₇—C₆H₄— | 7 | H— | CH₃— | 0 | 210.4 |
| 175 | 26 | H— | —CH=CH— | 3Cl—C₆H₄— | 6 | H— | H— | 1 | 253.0 |
| 176 | 31 | H— | —CH=CH— | 3Cl—C₆H₄— | 6 | H— | H— | 0 | 215.2 |
| 177 | 21 | H— | —CH=CH— | 3Cl—C₆H₄— | 6 | H— | i-C₄H₉— | 0 | 209.7 |
| 178 | 21 | H— | —CH=CH— | 3Cl—C₆H₄— | 7 | H— | i-C₄H₉— | 0 | 187.5 |
| 179 | 23 | H— | —CH=CH— | 3Cl—C₆H₄— | 6 | H— | C₃H₇— | 0 | 204.1 |
| 180 | 23 | H— | —CH=CH— | 3Cl—C₆H₄— | 7 | H— | C₃H₇— | 0 | 188.8 |
| 181 | 21 | H— | —CH=CH— | 3Cl—C₆H₄— | 6 | H— | i-C₃H₇— | 0 | — |
| 182 | 26 | H— | —CH=CH— | c.C₆H₁₁— | 6 | H— | H— | 0 | 275.7 |
| 183 | 31 | H— | —CH=CH— | c.C₆H₁₁— | 6 | H— | H— | 1 | — |
| 184 | 26 | H— | —CH=CH— | 4-Cl—C₆H₄— | 6 | H— | H— | 1 | 149.2 |
| 185 | 31 | H— | —CH=CH— | 4-Cl—C₆H₄— | 6 | H— | H— | 1 | — |
| 186 | 26 | H— | —CH=CH— | c.C₅H₉— | 6 | H— | H— | 1 | 229.5 |
| 187 | 31 | H— | —CH=CH— | c.C₅H₉— | 6 | H— | H— | 1 | 236.1 |
| 188 | 28 | H— | —CH=CH— | 3-Cl—C₆H₄— | 6 | H— | C₆H₅— | 0 | — |
| 189 | 26 | H— | —CH=CH— | CH₃— | 6 | H— | H— | 0 | 263.8 |
| 190 | 31 | H— | —CH=CH— | CH₃— | 6 | H— | H— | 0 | 216.5 |
| 191 | 23 | H— | —CH=CH— | 4Cl—C₆H₄— | 6 | H— | C₃H₇— | 0 | 222.0 |
| 192 | 23 | H— | —CH=CH— | 4Cl—C₆H₄— | 7 | H— | C₃H₇— | 0 | 200.3 |
| 193 | 21 | H— | —CH=CH— | 4Cl—C₆H₄— | 6 | H— | —CH₂—CH(CH₃)₂ | 0 | 203.9 |
| 194 | 21 | H— | —CH=CH— | 4Cl—C₆H₄— | 7 | H— | —CH₂—CH(CH₃)₂ | 0 | 200.9 |
| 195 | 21 | H— | —CH=CH— | 4Cl—C₆H₄— | 6 | H— | i-C₃H₇— | 0 | 245.5 |
| 196 | 30 | H— | —CH=CH— | 3Cl—C₆H₄— | 6 | H— | C₆H₅— | 0 | — |
| 197 | 26 | H— | —CH=CH— | C₂H₅— | 6 | H— | H— | 0 | 200.6 |
| 198 | 31 | H— | —CH=CH— | C₂H₅— | 6 | H— | H— | 1 | 186.5/0.5H₂O |
| 199 | 25 | H— | —CH=CH— | C₆H₅— | 6 | H— | C₆H₅—CO— | 1 | — |
| 200 | 26 | H— | —CH=CH— | 4F—C₆H₄— | 6 | H— | H— | 1 | 259.5 |
| 201 | 31 | H— | —CH=CH— | 4F—C₆H₄— | 6 | H— | H— | 0 | — |
| 202 | 26 | H— | —CH=CH— | 2F—C₆H₄— | 6 | H— | H— | 1 | 220.3 |
| 203 | 31 | H— | —CH=CH— | 3F—C₆H₄— | 6 | H— | H— | 0 | — |
| 204 | 26 | H— | —CH=CH— | 4Cl—C₆H₄— | 6 | H— | H— | 1 | 135.4/0.5H₂O |
| 205 | 31 | H— | —CH=CH— | 3Cl—C₆H₄— | 6 | H— | H— | 0 | — |
| 206 | 34 | H— | —CH=CH— | i-C₃H₇— | 6 | NH₂— | CH₃— | 0 | — |
| 207 | 28 | H— | —CH=N— | C₆H₅— | 6 | H— | C₆H₅— | 0 | 259.3 |
| 208 | 30 | H— | —CH=N— | C₆H₅— | 6 | H— | C₆H₅— | 0 | — |
| 209 | 28 | H— | —CH=CH— | i-C₃H₇— | 6 | H— | 2CH₃—C₆H₄— | 0 | 154.2/0.5H₂O |
| 210 | 30 | H— | —CH=CH— | i-C₃H₇— | 6 | H— | 2CH₃—C₆H₄— | 0 | — |
| 211 | 27 | H— | —CH=CH— | i-C₃H₇— | 6 | H— | 3-OCH₃—C₆H₄— | 1 | — |

TABLE 9-continued

| Comp. No. | Ex. No. | R | $-X^1=X^2-$ | Y | p | $R^3$ | $R^4$ | n | mp.(°C.)/ base/salt |
|---|---|---|---|---|---|---|---|---|---|
| 212 | 30 | H | $-CH=CH-$ | $i-C_3H_7$ | 6 | H | $3-OCH_3-C_6H_4-$ | 0 | 225.0 |
| 213 | 27 | H | $-CH=CH-$ | $i-C_3H_7$ | 6 | H | $2F-C_6H_4-$ | 1 | — |
| 214 | 30 | H | $-CH=CH-$ | $i-C_3H_7$ | 6 | H | $2F-C_6H_4-$ | 0 | 230.1 |
| 215 | 27 | H | $-CH=N-$ | $i-C_3H_7$ | 6 | H | $4F-C_6H_4-$ | 1 | — |
| 216 | 30 | H | $-CH=N-$ | $i-C_3H_7$ | 6 | H | $4F-C_6H_4-$ | 0 | 268.0 |
| 217 | 28 | H | $-CH=CH-$ | $i-C_3H_7$ | 6 | H | $4-CH_3-C_6H_4-$ | 1 | — |
| 218 | 30 | H | $-CH=CH-$ | $i-C_3H_7$ | 6 | H | $4-CH_3-C_6H_4-$ | 0 | 221.9 |
| 219 | 27 | H | $-CH=N-$ | $i-C_3H_7$ | 6 | H | $3F-C_6H_4-$ | 1 | — |
| 220 | 30 | H | $-CH=N-$ | $i-C_3H_7$ | 6 | H | $3F-C_6H_4-$ | 0 | 202.3 |
| 221 | 27 | H | $-CH=N-$ | $i-C_3H_7$ | 6 | H | $4Cl-C_6H_4-$ | 1 | — |
| 222 | 30 | H | $-CH=N-$ | $i-C_3H_7$ | 6 | H | $4Cl-C_6H_4-$ | 0 | 274.6 |
| 223 | 27 | $CH_3-$ | $-CH=CH-$ | $i-C_3H_7$ | 6 | H | $C_6H_5-$ | 1 | — |
| 224 | 30 | $CH_3-$ | $-CH=CH-$ | $i-C_3H_7$ | 6 | H | $C_6H_5-$ | 0 | 252.5 |
| 225 | 27 | H | $-CH=CH-$ | $i-C_3H_7$ | 6 | H | $4-Br-C_6H_4-$ | 1 | — |
| 226 | 30 | H | $-CH=CH-$ | $i-C_3H_7$ | 6 | H | $4-Br-C_6H_4-$ | 0 | 226.0 |
| 227 | 27 | H | $-CH=CH-$ | $i-C_3H_7$ | 6 | H | $3,4-F_2-C_6H_3-$ | 1 | — |
| 228 | 30 | H | $-CH=CH-$ | $i-C_3H_7$ | 6 | H | $3,4-F_2-C_6H_3-$ | 0 | 218.0 |
| 229 | 27 | H | $-CH=CH-$ | $i-C_3H_7$ | 6 | H | $3CH_3-C_6H_4-$ | 1 | — |
| 230 | 30 | H | $-CH=CH-$ | $i-C_3H_7$ | 6 | H | $3CH_3-C_6H_4-$ | 0 | 230.4 |
| 231 | 27 | H | $-CH=CH-$ | $i-C_3H_7$ | 6 | H | $4-OCH_3-C_6H_4-$ | 1 | — |
| 232 | 30 | H | $-CH=CH-$ | $i-C_3H_7$ | 6 | H | $4-OCH_3-C_6H_4-$ | 0 | 157.8/$H_2O$ |
| 233 | 27 | H | $-CH=CH-$ | $3,4Cl_2-C_6H_3-$ | 6 | H | $C_6H_5-$ | 1 | — |
| 234 | 30 | H | $-CH=CH-$ | $3,4Cl_2-C_6H_3-$ | 6 | H | $C_6H_5-$ | 0 | 262.5 |
| 235 | 27 | H | $-CH=CH-$ | $i-C_3H_7$ | 6 | H | $3,4(OCH_3)_2-C_6H_3-$ | 1 | — |
| 236 | 32 | H | $-CH=CH-$ | $i-C_3H_7$ | 6 | H | $3,4(OCH_3)_2-C_6H_3-$ | 0 | 242.6 |
| 237 | 27 | H | $-CH=CH-$ | $i-C_3H_7$ | 6 | H | $2,4Cl_2-C_6H_3-$ | 1 | — |
| 238 | 32 | H | $-CH=CH-$ | $i-C_3H_7$ | 6 | H | $2,4Cl_2-C_6H_3-$ | 0 | 178.0 |
| 239 | 27 | H | $-CH=CH-$ | $i-C_3H_7$ | 6 | H | 2-naphthalenyl- | 1 | — |
| 240 | 32 | H | $-CH=CH-$ | $i-C_3H_7$ | 6 | H | 2-naphthalenyl- | 0 | 274.9 |
| 241 | 27 | H | $-CH=CH-$ | $i-C_3H_7$ | 6 | H | $3,4,5(OCH_3)_3-C_6H_2-$ | 1 | — |
| 242 | 32 | H | $-CH=CH-$ | $i-C_3H_7$ | 6 | H | $3,4,5(OCH_3)_3-C_6H_2-$ | 0 | 266.6 |
| 243 | 27 | H | $-CH=N-$ | $i-C_3H_7$ | 6 | H | 3-thienyl- | 1 | — |
| 244 | 32 | H | $-CH=N-$ | $i-C_3H_7$ | 6 | H | 3-thienyl- | 0 | 269.9 |
| 245 | 27 | H | $-CH=CH-$ | $i-C_3H_7$ | 6 | H | 2-thienyl- | 1 | — |
| 246 | 32 | H | $-CH=CH-$ | $i-C_3H_7$ | 6 | H | 2-thienyl- | 0 | 276.0 |
| 247 | 27 | H | $-CH=CH-$ | $i-C_3H_7$ | 6 | H | $2-OCH_3-C_6H_4-$ | 1 | — |
| 248 | 32 | H | $-CH=CH-$ | $i-C_3H_7$ | 6 | H | $2-OCH_3-C_6H_4-$ | 0 | 169.8 |
| 249 | 27 | H | $-CH=CH-$ | $i-C_3H_7$ | 6 | H | 1-naphthalenyl- | 1 | — |
| 250 | 32 | H | $-CH=CH-$ | $i-C_3H_7$ | 6 | H | 1-naphthalenyl- | 0 | 183.5 |

TABLE 9-continued

| Comp. No. | Ex. No. | R | $-X^1=X^2-$ | Y | p | $R^3$ | $R^4$ | n | mp.(°C.)/ base/salt |
|---|---|---|---|---|---|---|---|---|---|
| 251 | 27 | H— | —CH=CH— | i-C₃H₇ | 6 | H— | 4-OC₂H₅—C₆H₄— | 1 | — |
| 252 | 32 | H— | —CH=CH— | i-C₃H₇ | 6 | H— | 4-OC₂H₅—C₆H₄— | 0 | 129.5 |
| 253 | 27 | H— | —CH=CH— | i-C₃H₇ | 6 | H— | 2-Cl—C₆H₄— | 1 | 172.5 |
| 254 | 32 | H— | —CH=CH— | i-C₃H₇ | 6 | H— | 2-Cl—C₆H₄— | 0 | — |
| 255 | 27 | H— | —CH=CH— | i-C₃H₇ | 6 | H— | 3-OH—C₆H₄— | 1 | 252.6 |
| 256 | 32 | H— | —CH=CH— | i-C₃H₇ | 6 | H— | 3-OH—C₆H₄— | 0 | 157.8/0.5H₂O |
| 257 | 27 | H— | —CH=CH— | i-C₃H₇ | 6 | H— | 3-Br—C₆H₄— | 1 | 298.7 |
| 258 | 32 | H— | —CH=CH— | i-C₃H₇ | 6 | H— | 3-Br—C₆H₄— | 0 | 188.5 |
| 259 | 20 | H— | —CH=CH— | i-C₃H₇ | 7 | H— | 3-pyridinyl- | 0 | — |
| 260 | 23 | H— | —CH=N— | i-C₃H₇ | 7 | H— | 3-thienyl- | 0 | 273.1 |
| 261 | 27 | H— | —CH=CH— | i-C₃H₇ | 6 | H— | 3-thienyl- | 1 | 187.3 |
| 262 | 32 | H— | —CH=CH— | i-C₃H₇ | 6 | H— | 3-thienyl- | 0 | 194.8 |
| 263 | 23 | H— | —CH=N— | i-C₃H₇ | 6 | H— | C₃H₇ | 0 | — |
| 264 | 23 | H— | —CH=N— | i-C₃H₇ | 6 | H— | C₂H₅ | 0 | — |
| 265 | 27 | H— | —CH=CH— | i-C₃H₇ | 6 | H— | 2-thienyl- | 1 | >300(dec.) |
| 266 | 32 | H— | —CH=CH— | i-C₃H₇ | 6 | H— | 2-thienyl- | 0 | 165.4 |
| 267 | 27 | H— | —CH=CH— | i-C₃H₇ | 6 | H— | 2Cl—6F—C₆H₃— | 1 | — |
| 268 | 32 | H— | —CH=CH— | i-C₃H₇ | 6 | H— | 2Cl—6F—C₆H₃— | 0 | 241.4 |
| 269 | 27 | H— | —CH=CH— | i-C₃H₇ | 6 | H— | 3Br—4OH—C₆H₃— | 1 | 294.2 |
| 270 | 32 | H— | —CH=CH— | i-C₃H₇ | 6 | H— | 3Br—4OH—C₆H₃— | 0 | — |
| 271 | 20 | H— | —CH=CH— | i-C₃H₇ | 7 | H— | 3-pyridinyl- | 0 | 272.0 |
| 272 | 27 | H— | —CH=CH— | C₂H₅ | 6 | H— | C₆H₅— | 1 | — |
| 273 | 32 | H— | —CH=CH— | C₂H₅ | 6 | H— | C₆H₅— | 0 | 220.1 |
| 274 | 27 | H— | —CH=CH— | i-C₄H₉ | 6 | H— | C₆H₅— | 1 | — |
| 275 | 32 | H— | —CH=CH— | i-C₃H₇ | 6 | H— | 4F—C₆H₄— | 0 | 250.0 |
| 276 | 27 | H— | —N=CH— | i-C₃H₇ | 6 | H— | 4F—C₆H₄— | 1 | — |
| 277 | 27 | H— | —CH=CH— | C₄H₉ | 6 | H— | 3F—C₆H₄— | 1 | 132.9 |
| 278 | 27 | H— | —CH=CH— | C₄H₉ | 6 | H— | 3F—C₆H₄— | 0 | 163.9/0.5H₂O |
| 279 | 32 | H— | —CH=CH— | i-C₃H₇ | 7 | H— | C₂H₅ | 0 | — |
| 280 | 23 | H— | —CH=N— | i-C₃H₇ | 6 | H— | 3Cl—4OH—C₆H₃— | 1 | 237.0 |
| 281 | 27 | H— | —CH=CH— | i-C₃H₇ | 6 | H— | 3Cl—4OH—C₆H₃— | 0 | 236.3 |
| 282 | 32 | H— | —CH=CH— | i-C₃H₇ | 6 | H— | 3-pyridinyl- | 1 | — |
| 283 | 20 | H— | —CH=CH— | i-C₃H₇ | 6 | H— | C₆H₅— | 1 | 210.2 |
| 284 | 27 | H— | —CH=CH— | i-C₃H₇ | 6 | H— | C₆H₅— | 0 | — |
| 285 | 27 | H— | —CH=CH— | i-C₃H₇ | 6 | H— | 2-CH₃—C₆H₄— | 1 | 230.8 |
| 286 | 32 | H— | —N=CH— | C₃H₇ | 6 | H— | 2-CH₃—C₆H₄— | 0 | — |
| 287 | 27 | H— | —CH=N— | C₃H₇ | 6 | H— | 3Cl—C₆H₄— | 1 | — |
| 288 | 32 | H— | —N=CH— | i-C₃H₇ | 6 | H— | 3Cl—C₆H₄— | 1 | 176.7 |
| 289 | 32 | H— | —N=CH— | i-C₃H₇ | 6 | H— | C₆H₄— | 0 | — |

TABLE 9-continued

| Comp. No. | Ex. No. | R | —X$^1$=X$^2$— | Y | p | R$^3$ | R$^4$ | n | mp.(°C.)/ base/salt |
|---|---|---|---|---|---|---|---|---|---|
| 290 | 27 | H— | —CH=N— | i-C$_4$H$_9$— | 6 | H— | 2CH$_3$—C$_6$H$_4$— | 1 | — |
| 291 | 32 | H— | —CH=N— | i-C$_4$H$_9$— | 6 | H— | 2CH$_3$—C$_6$H$_4$— | 0 | 168.3 |
| 292 | 27 | H— | —CH=N— | C$_2$H$_5$— | 6 | H— | 2CH$_3$—C$_6$H$_4$— | 1 | 187.0 |
| 293 | 32 | H— | —CH=N— | C$_2$H$_5$— | 6 | H— | 2CH$_3$—C$_6$H$_4$— | 0 | 183.6 |
| 294 | 27 | H— | —CH=N— | i-C$_3$H$_7$— | 6 | H— | 3Cl—C$_6$H$_4$— | 1 | — |
| 295 | 32 | H— | —CH=N— | i-C$_3$H$_7$— | 6 | H— | 3Cl—C$_6$H$_4$— | 0 | 213.2 |
| 296 | 27 | H— | —N=CH— | i-C$_3$H$_7$— | 6 | H— | 3F—C$_6$H$_4$— | 1 | — |
| 297 | 32 | H— | —N=CH— | i-C$_3$H$_7$— | 6 | H— | 3F—C$_6$H$_4$— | 0 | 125.8 |
| 298 | 27 | H— | —CH=N— | i-C$_3$H$_7$— | 6 | H— | 2F—C$_6$H$_4$— | 1 | — |
| 299 | 32 | H— | —CH=N— | i-C$_3$H$_7$— | 6 | H— | 2F—C$_6$H$_4$— | 0 | 183.3 |
| 300 | 27 | H— | —CH=N— | C$_4$H$_9$— | 6 | H— | C$_6$H$_5$— | 1 | — |
| 301 | 32 | H— | —CH=N— | C$_4$H$_9$— | 6 | H— | C$_6$H$_5$— | 0 | 176.4 |
| 302 | 27 | H— | —CH=N— | C$_4$H$_9$— | 6 | H— | 2-CH$_3$—C$_6$H$_4$— | 1 | — |
| 303 | 32 | H— | —CH=N— | C$_4$H$_9$— | 6 | H— | 2-CH$_3$—C$_6$H$_4$— | 0 | 210.5 |
| 304 | 27 | H— | —CH=N— | C$_3$H$_7$— | 6 | H— | 3F—C$_6$H$_4$— | 1 | — |
| 305 | 32 | H— | —CH=N— | C$_3$H$_7$— | 6 | H— | 3F—C$_6$H$_4$— | 0 | 206.3 |
| 306 | 27 | H— | —CH=N— | C$_3$H$_7$— | 6 | H— | C$_6$H$_5$— | 1 | — |
| 307 | 32 | H— | —CH=N— | C$_3$H$_7$— | 6 | H— | C$_6$H$_5$— | 0 | 202.2 |
| 308 | 27 | H— | —CH=CH— | C$_3$H$_7$— | 6 | H— | 2-CH$_3$—C$_6$H$_4$— | 1 | — |
| 309 | 32 | H— | —CH=CH— | C$_2$H$_5$— | 6 | H— | 2-CH$_3$—C$_6$H$_4$— | 0 | — |
| 310 | — | H— | —N=CH— | i-C$_3$H$_7$— | 6 | C$_6$H$_5$—CH$_2$— | CH$_3$— | 0 | — |
| 311 | — | H— | —CH=CH— | 1H-imidazolyl | 6 | H— | CH$_3$— | 0 | — |
| 312 | — | H— | —CH=CH— | i-C$_3$H$_7$— | 7 | H— | CH$_3$— | 0 | — |
| 313 | — | H— | —CH=CH— | 3Cl—C$_6$H$_4$— | 7 | H— | i-C$_3$H$_7$— | 0 | — |
| 314 | — | H— | —CH=CH— | i-C$_3$H$_7$— | 7 | H— | C$_2$H$_5$— | 0 | — |

*: —CH(CH$_3$)COOC$_2$H$_5$

TABLE 10

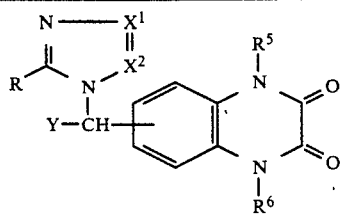

| Comp. No. | Ex. No. | R | X¹=X² | Y | p | R⁵ | R⁶ | mp.(°C.)/ base/salt |
|---|---|---|---|---|---|---|---|---|
| 315 | 29 | H— | CH=CH | H— | 6 | H— | H— | >300 |
| 316 | — | H— | CH=CH | $C_6H_5$— | 6 | $CH_3$— | $CH_3$— | — |
| 317 | — | H— | CH=CH | i-$C_3H_7$— | 6 | $CH_3$— | $CH_3$— | — |

C. PHARMACOLOGICAL EXAMPLES

The useful pharmacological properties of the compounds of the present invention can for example be demonstrated by the following experiment.

EXAMPLE 39

Metabolism of exogenously administered all-trans-retinoic acid

Male Wistar rats weighing 200~210 g were orally treated with vehicle (PEG 200) or with 40 mg/kg of a compound of formula (I). One hour later, the animals were anesthetized with ether and injected intrajugularly with 0.50 ml saline solution containing 20 μg of all-trans-retinoic acid. Two hours after this injection, rats were killed by decapitation and blood was collected on heparin. Blood samples were centrifuged (1000 g, 15 min) and plasma was recovered to determine the quantity of plasmatic all-trans-retinoic acid. The samples were analyzed by means of HPLC with UV-detection at 350 nm. Quantification was achieved by peak area integration and external standardization. Under the conditions used, plasma concentrations of the retinoic acid in vehicle-pretreated animals were not detectable (<0.5 ng/ml), whereas compound nos. 5, 9, 11, 12, 13, 15, 16, 18, 57, 68, 69, 70, 86, 89, 94, 97, 103, 123, 132, 133, 134, 141, 146, 147, 148, 149, 151, 157, 161, 181, 183, 187, 198, 201, 210, 262, 263, 264, 295 and 299 enhanced the recovery of all-trans-retinoic acid from the plasma to at least 10 ng/ml after dosing with 40 mg/kg. The following compounds even enhanced the recovery of all trans-retinoic acid from the plasma to at least 20 ng/ml after dosing with 40 mg/kg: compound nos. 12, 70, 77, 86, 138 and 146.

EXAMPLE 40

Metabolism of endogenously administered all-trans-retinoic acid

Male Wistar rats weighing 200~210 g were orally treated with vehicle (PEG 200) or with 40 mg/kg of a compound of formula (I). Two hours after drug administration, the rats were killed by decapitation and blood was collected on heparin. Blood samples were centrifuged (1000 g, 15 min) and plasma was recovered to determine the quantity of plasmatic all-trans-retinoic acid. The samples were analyzed by means of HPLC with UV-detection at 350 nm. Quantification was achieved by peak area integration and external standardization. Under the conditions used, plasma concentrations of the retinoic acid in vehicle-pretreated animals were not detectable (<0.5 ng/ml), whereas compound nos. 5, 77, 94, 127, 151, 170, 183, 187, 190, 197, 201, 205, 208, 210, 212, 216, 218, 232, 246, 259, 260, 262, 263, 264, 266, 271, 273, 275, 277, 279, 280, 285, 287, 289, 291, 293, 295, 299, 301, 307 and 309 enhanced the recovery of all-trans-retinoic acid from the plasma to at least 1 ng/ml.

We claim:
1. A compound having the formula

(I)

or a pharmaceutically acceptable acid addition salt thereof and the stereochemically isomeric form thereof, wherein —$X^1$=$X^2$— is a bivalent radical having the formula —CH=CH—      (x), —CH=N—      (y), or —N=CH—      (z);

R is hydrogen or $C_{1-6}$alkyl;
Y is hydrogen; $C_{1-10}$alkyl; $C_{3-7}$cycloalkyl; $Ar^1$; $Ar^2$-$C_{1-6}$alkyl; $C_{2-6}$alkenyl or $C_{2-6}$alkynyl;
Z is a radical of formula

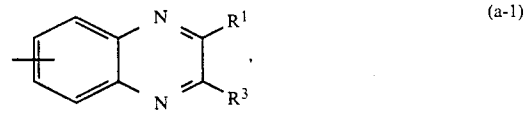

(a-1)

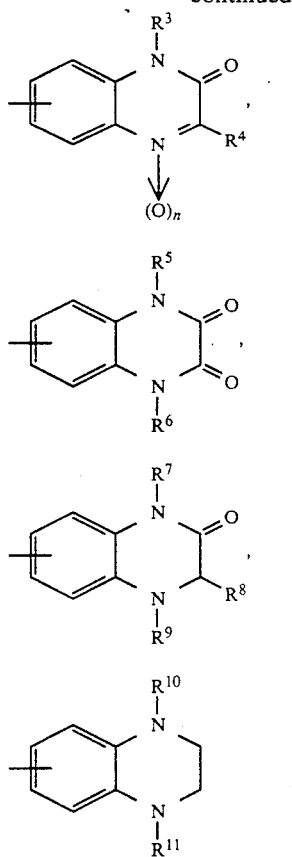

wherein
R¹ is hydrogen, halo, $C_{1-6}$alkyl, $C_{1-6}$alkyloxy, amino, mono- or di($C_{1-6}$alkyl)amino, $Ar^2$ or imidazolyl;

R² is hydrogen, $C_{1-6}$alkyl or $Ar^1$;

R³ and R⁷ each independently are hydrogen, $C_{1-6}$alkyl, $Ar^2$-$C_{1-6}$alkyl, amino or mono ($C_{1-6}$alkyl)amino;

R⁴ and R⁸ each independently are $C_{1-6}$alkyl, $Ar^1$, $C_{1-6}$alkylcarbonyl, $Ar^2$-carbonyl, $C_{1-6}$alkyloxycarbonyl, carboxyl, $C_{1-6}$alkyloxycarbonyl$C_{1-4}$alkyl, aminocarbonyl or cyano;

R⁵, R⁶, R⁹, R¹⁰ and R¹¹ each independently are hydrogen, $C_{1-6}$alkyl or $Ar^2$-$C_{1-6}$alkyl;

n is 0 or 1; and $Ar^1$ is phenyl, substituted phenyl, naphthalenyl, pyridinyl, imidazolyl, triazolyl, thienyl, furanyl or thiazolyl and $Ar^2$ is phenyl or substituted phenyl; and substituted phenyl in $Ar^1$ or $Ar^2$ being phenyl substituted with 1, 2 or 3 substituents each independently selected from halo, hydroxy, trifluoromethyl, $C_{1-6}$alkyl, $C_{1-6}$alkyloxy, cyano, amino, mono- and di($C_{1-6}$alkyl)amino, nitro, carboxyl, formyl and $C_{1-6}$alkyloxycarbonyl.

2. A compound according to claim 1 wherein R is hydrogen or $C_{1-4}$alkyl; Y is hydrogen, $C_{1-6}$alkyl, $C_{3-7}$cycloalkyl, phenyl, substituted phenyl, pyridinyl, imidazolyl or thienyl; Z is a radical of formula (a-1), (a-2), (a-3), (a-4) or (a-5) wherein R¹ is hydrogen, $C_{1-4}$alkyl, halo, $C_{1-4}$alkyloxy, amino, mono- or di($C_{1-4}$alkyl)amino, phenyl, substituted phenyl or imidazolyl; R² is hydrogen, $C_{1-4}$alkyl, phenyl or substituted phenyl; R³ is hydrogen, $C_{1-4}$alkyl, amino, $C_{1-4}$alkylamino or $C_{1-4}$alkyl substituted with phenyl or substituted phenyl; R⁴ is hydrogen, $C_{1-4}$alkyl, $C_{1-4}$alkyloxyarbonyl$C_{1-4}$alkyl, phenyl, substituted phenyl, carboxyl, $C_{1-4}$alkyloxycarbonyl, carboxyl, phenylcarbonyl, substituted phenylcarbonyl, naphthalenyl, thienyl, furanyl, pyridinyl or imidazolyl; R⁵ and R⁶ each independently are hydrogen or $C_{1-4}$alkyl; R⁷ is hydrogen, $C_{1-4}$alkyl, amino or $C_{1-4}$alkyl substituted with phenyl or substituted phenyl; R⁸ is hydrogen, $C_{1-4}$alkyl, phenyl, substituted phenyl, $C_{3-7}$cycloalkyl, naphthalenyl, thienyl, pyridinyl or imidazolyl; R⁹ is hydrogen or $C_{1-4}$ alkyl and R¹⁰ and R¹¹ are hydrogen.

3. A compound according to claim 2 wherein $-X^1=X^2-$ is a radical having the formula (x) or (y); R is hydrogen; and Y is hydrogen, $C_{1-4}$alkyl, cyclopropyl, cyclopentyl, cyclohexyl, imidazolyl, thienyl, pyridinyl or phenyl optionally substituted with one or two substituents selected from halo, $C_{1-4}$alkyl, $C_{1-4}$alkyloxy and trifluoromethyl.

4. A compound according to claim 3 wherein Z is a radical of formula (a-1) wherein R¹ is hydrogen, $C_{1-4}$alkyl, $C_{1-4}$alkyloxy, halo, amino, di($C_{1-4}$alkyl)amino, phenyl or imidazolyl, R² is hydrogen, $C_{1-4}$alkyl or phenyl and Y is hydrogen, $C_{1-4}$alkyl, thienyl, imidazolyl or phenyl optionally substituted with one or two substituents selected from halo, $C_{1-4}$alkyl, $C_{1-4}$alkyloxy or trifluoromethyl; or Z is a radical of formula (a-2) wherein R³ is hydrogen, $C_{1-4}$alkyl, amino or $C_{1-4}$alkyl substituted with phenyl and R⁴ is hydrogen, $C_{1-4}$alkyl, carboxyl, $C_{1-4}$alkyloxycarbonyl, naphthalenyl, thienyl, pyridinyl, imidazolyl, phenyl or phenyl substituted with 1, 2 or 3 substituents each independently selected from $C_{1-4}$alkyl, $C_{1-4}$alkyloxy, halo, hydroxy and trifluoromethyl and Y is hydrogen, $C_{1-4}$alkyl, cyclopropyl, cyclopentyl, cyclohexyl, imidazolyl, thienyl, pyridinyl or phenyl optionally substituted with one or two substituents selected from halo, $C_{1-4}$alkyl, $C_{1-4}$alkyloxy and trifluoromethyl.

5. A compound according to claim 1 wherein Z is a radical of formula (a-1); $-X^1=X^2-$ is a radical having the formula (x) or (y); R is hydrogen; R¹ and R² are both hydrogen and Y is phenyl, halophenyl or thienyl.

6. A compound according to claim 1 wherein Z is a radical of formula (a-2); $-X^1=X^2-$ is a radical of formula (x) or (y); R is hydrogen; Y is hydrogen, $C_{1-4}$alkyl, cyclopropyl, cyclopentyl or cyclohexyl; R³ is hydrogen; R⁴ is hydrogen, $C_{1-4}$alkyl, naphthalenyl, thienyl, pyridinyl, imidazolyl, phenyl or phenyl substituted with 1 or 2 substituents each independently selected from methyl, halo, hydroxy and methoxy; and n is 0.

7. A compound according to claim 1 wherein Z is a radical of formula (a-2); $-X^1=X^2-$ is a radical of formula (x) or (y); R is hydrogen; Y is phenyl or halophenyl; R³ is hydrogen; R⁴ is hydrogen or $C_{1-4}$alkyl and n is 0.

8. A compound according to claim 1 wherein the compound is 6-[(1H-imidazol-1-yl) phenylmethyl]-quinoxaline and 6-[(4-fluorophenyl) (1H-imidazol-1-yl)methyl]quinoxaline, a pharmaceutically acceptable acid addition salt or a possible stereoisomeric form thereof.

9. A compound according to claim 1 wherein the compound is 6-[1-(1H-imidazol-1-yl)-2-methylpropyl]-3-phenyl-2(1H)-quinoxalinone, 6-[1-(1H-imidazol-1-yl)-2-methylpropyl]-3-propyl-2(1H)-quinoxalinone, 3-(3-fluorophenyl)-6-[1-(1H-imidazol-1-yl)-2-methylpropyl]-

2(1H)-quinoxalinone, a pharmaceutically acceptable acid addition salt or a possible stereoisomer thereof.

10. A retinoid metabolism inhibiting composition comprising an inert carrier and as active ingredient an effective amount of a compound as defined in claim 1.

11. A composition according to claim 10 wherein R is hydrogen or $C_{1-4}$alkyl; Y is hydrogen, $C_{1-6}$alkyl, $C_{3-7}$cycloalkyl, phenyl, substituted phenyl, pyridinyl, imidazolyl or thienyl; Z is a radical of formula (a-1), (a-2), (a-3), (a-4) or (a-5) wherein $R^1$ is hydrogen, $C_{1-4}$alkyl, halo, $C_{1-4}$alkyloxy, amino, mono- or di($C_{1-4}$alkyl)amino, phenyl, substituted phenyl or imidazolyl, $R^2$ is hydrogen, $C_{1-4}$alkyl, phenyl or substituted phenyl, $R^3$ is hydrogen, $C_{1-4}$alkyl, amino, $C_{1-4}$alkylamino or $C_{1-4}$alkyl substituted with phenyl or substituted phenyl; $R^4$ is hydrogen, $C_{1-4}$alkyl, $C_{1-4}$alkyloxyarbonyl$C_{1-4}$alkyl, phenyl, substituted phenyl, carboxyl, $C_{1-4}$alkyloxycarbonyl, carboxyl, phenylcarbonyl, substituted phenylcarbonyl, naphthalenyl, thienyl, furanyl, pyridinyl or imidazolyl; $R^5$ and $R^6$ each independently are hydrogen or $C_{1-4}$alkyl; $R^7$ is hydrogen, $C_{1-4}$alkyl, amino or $C_{1-4}$alkyl substituted with phenyl or substituted phenyl; $R^8$ is hydrogen, $C_{1-4}$alkyl, phenyl, substituted phenyl, $C_{3-7}$ cycloalkyl, naphthalenyl, thienyl, pyridinyl or imidazolyl; $R^9$ is hydrogen or $C_{1-4}$alkyl and $R^{10}$ and $R^{11}$ are hydrogen.

12. A composition according to claim 12 wherein $-X^1=X^2-$ is a radical having the formula (x) or (y); R is hydrogen; and Y is hydrogen, $C_{1-4}$alkyl, cyclopropyl, cyclopentyl, cyclohexyl, imidazolyl, thienyl, pyridinyl or phenyl optionally substituted with one or two substituents selected from halo, $C_{1-4}$alkyl, $C_{1-4}$alkyloxy and trifluoromethyl.

13. A composition according to claim 12 wherein

Z is a radical of formula (a-1) wherein $R^1$ is hydrogen, $C_{1-4}$alkyl, $C_{1-4}$alkyloxy, halo, amino, di($C_{1-4}$alkyl)amino, phenyl or imidazolyl, $R^2$ is hydrogen, $C_{1-4}$alkyl or phenyl and Y is hydrogen, $C_{1-4}$alkyl, thienyl, imidazolyl or phenyl optionally substituted with one or two substituents selected from halo, $C_{1-4}$alkyl, $C_{1-4}$alkyloxy or trifluoromethyl; or Z is a radical of formula (a-2) wherein $R^3$ is hydrogen, $C_{1-4}$alkyl, amino or $C_{1-4}$alkyl substituted with phenyl and $R^4$ is hydrogen, $C_{1-4}$alkyl, carboxyl, $C_{1-4}$alkyloxycarbonyl, naphthalenyl, thienyl, pyridinyl, imidazolyl, phenyl or phenyl substituted with 1, 2 or 3 substituents each independently selected from $C_{1-4}$alkyl, $C_{1-4}$alkyloxy, halo, hydroxy and trifluoromethyl and Y is hydrogen, $C_{1-4}$alkyl, cyclopropyl, cyclopentyl, cyclohexyl, imidazolyl, thienyl, pyridinyl or phenyl optionally substituted with one or two substituents selected from halo, $C_{1-4}$alkyl, $C_{1-4}$alkyloxy and trifluoromethyl.

* * * * *

UNITED STATES PATENT AND TRADEMARK OFFICE
CERTIFICATE OF CORRECTION

PATENT NO. : 5,028,606

DATED : July 2, 1991

INVENTOR(S) : Venet et al.

It is certified that error appears in the above-identified patent and that said Letters Patent is hereby corrected as shown below:

Column 1, line 58, formula a-1, "$R^3$" should be --$R^2$--.

Column 58, line 67, formula a-1, "$R^3$" should be --$R^2$--.

Signed and Sealed this

First Day of June, 1993

Attest:

MICHAEL K. KIRK

Attesting Officer

Acting Commissioner of Patents and Trademarks